US007989179B2

(12) United States Patent
Terasaka et al.

(10) Patent No.: US 7,989,179 B2
(45) Date of Patent: Aug. 2, 2011

(54) LXR LIGAND TESTING METHOD

(75) Inventors: Naoki Terasaka, Saitama (JP); Shoko Honzumi, Tokyo (JP); Ira Glenn Schulman, San Diego, CA (US); Brandee Lynn Wagner, San Diego, CA (US); Patricia J. Willy, San Diego, CA (US)

(73) Assignee: Daiichi Sankyo Company, Limited, Tokyo (JP)

(*) Notice: Subject to any disclaimer, the term of this patent is extended or adjusted under 35 U.S.C. 154(b) by 422 days.

(21) Appl. No.: 11/921,967

(22) PCT Filed: Jun. 26, 2006

(86) PCT No.: PCT/US2006/024945
§ 371 (c)(1),
(2), (4) Date: Dec. 11, 2007

(87) PCT Pub. No.: WO2007/002654
PCT Pub. Date: Jan. 4, 2007

(65) Prior Publication Data
US 2009/0098570 A1 Apr. 16, 2009

Related U.S. Application Data

(60) Provisional application No. 60/694,806, filed on Jun. 28, 2005.

(51) Int. Cl.
*C12Q 1/60* (2006.01)
(52) U.S. Cl. ........................................................ 435/11
(58) Field of Classification Search .................. None
See application file for complete search history.

(56) References Cited

U.S. PATENT DOCUMENTS

| 6,090,836 | A  | 7/2000  | Adams et al. |
| 6,316,503 | B1 | 11/2001 | Li et al. |
| 6,828,446 | B2 | 12/2004 | Chandrakumar et al. |
| 7,112,606 | B2 | 9/2006  | Jiao et al. |
| 7,247,748 | B2 | 7/2007  | Thompson et al. |
| 7,250,283 | B2 | 7/2007  | Spiegelman et al. |
| 2002/0037514 | A1 | 3/2002 | Klein et al. |
| 2003/0073614 | A1 | 4/2003 | Schulman et al. |
| 2003/0207898 | A1 | 11/2003 | Chandrakumar et al. |
| 2003/0220339 | A1 | 11/2003 | Jiao et al. |
| 2003/0228607 | A1 | 12/2003 | Wagner et al. |
| 2004/0072868 | A1 | 4/2004 | Collins et al. |
| 2004/0110947 | A1 | 6/2004 | Chandrakumar et al. |
| 2004/0254362 | A1 | 12/2004 | Spiegelman et al. |
| 2005/0014807 | A1 | 1/2005 | Adams et al. |
| 2005/0107444 | A1 | 5/2005 | Thompson et al. |
| 2005/0113580 | A1 | 5/2005 | Thompson et al. |
| 2005/0131014 | A1 | 6/2005 | Collini et al. |
| 2005/0261319 | A1 | 11/2005 | Deuschle et al. |
| 2005/0282908 | A1 | 12/2005 | Collins et al. |
| 2006/0041164 | A1 | 2/2006 | Thompson et al. |
| 2006/0058351 | A1 | 3/2006 | Diaz et al. |
| 2006/0094733 | A1 | 5/2006 | Boggs et al. |
| 2006/0189663 | A1 | 8/2006 | Holm |
| 2006/0270718 | A1 | 11/2006 | Jiao et al. |

FOREIGN PATENT DOCUMENTS

| EP | 1 407 774 A1 | 4/2004 |
| WO | WO 99/18124 A1 | 4/1999 |
| WO | WO 01/73434 A2 | 10/2001 |
| WO | WO 01/82917 A2 | 11/2001 |
| WO | WO 02/077229 A2 | 10/2002 |
| WO | WO 03/004613 A2 | 1/2003 |
| WO | WO 03/090869 A1 | 11/2003 |
| WO | WO 03/106435 A1 | 12/2003 |
| WO | WO 2005/019264 A2 | 3/2005 |
| WO | WO 2006/004030 A1 | 1/2006 |
| WO | WO 2006/046593 A1 | 5/2006 |

OTHER PUBLICATIONS

English-language International Preliminary Report on Patentability and Written Opinion of the International Searching Authority, dated Jan. 9, 2008 for International application PCT/US2006/024945 filed Jun. 26, 2006; Applicants: Daiichi Sankyo Company Limited.
Bowman Miao et al., "Raising HDL cholesterol without inducing hepatic steatosis and hypertriglyceridemia by a selective LXR modulator," *Journal of Lipid Research*, vol. 45, 2004, pp. 1410-1417.
Patricia D. Pelton et al., "Nuclear Receptors as Potential Targets for Modulating Reverse Cholesterol Transport," *Current Topics in Medicinal Chemistry*, Bentham Science Publishers, Hilversum, NL, vol. 5, No. 3, Jan. 1, 2005, pp. 265 to 281.
Deepak S. Lala, "The Liver X Receptors," *Current Opinion in Investigational Drugs, Pharmapress*, US, vol. 6, No. 9, Jan. 1, 2005, pp. 934 to 943.
Bodzioch et al., "The gene encoding ATP-binding cassette transporter 1 is mutated in Tangier disease," *Nature Genetics*, (1999), vol. 22, 347-351.
Laffitte et al., "Activation of liver X receptor improves glucose tolerance through coordinate regulation of glucose metabolism in liver and adipose tissue," *Proc. Natl. Acad. Sci. USA*, (2003), vol. 100, No. 9, 5419-5424.
Ijpenberg et al., "In vivo activation of PPAR target genes by RXR homodimers," *EMBO J.*, (2004), vol. 23, No. 10, 2083-2091.
Kim et al., "Activating Signal Cointegrator 2 Required for Liver Lipid Metbolism Mediated by Liver X Receptors in Mice," *Mol. Cell. Biol.*, (2003), vol. 23, No. 10, 3583-3592.
Huuskonen et al., "Role of p160 Coactivator Complex in the Activation of Liver X Receptor," *Arterioscler. Thromb. Vasc. Biol.*, (2004), 24, 703-708.

(Continued)

Primary Examiner — Michael Pak
(74) Attorney, Agent, or Firm — Holtz Holtz Goodman & Chick PC

(57) ABSTRACT

A method of easily measuring whether or not an LXR ligand has the function of effecting, e.g., increasing, plasma triglyceride concentration and/or LDL cholesterol concentration in a mammal by using the binding activity between LXR and a coactivator, and a method of identifying LXR ligands that do not have the function of effecting, e.g., increasing, plasma triglyceride concentration and/or LDL cholesterol concentration by using the binding activity between LXR and a coactivator.

14 Claims, No Drawings

OTHER PUBLICATIONS

Kawajiri et al., "Role of the LXXLL-Motif and Activation Function 2 Domain in Subcellular Localization of Dax-1 (Dosage-Sensitive Sex Reversal-Adrenal Hypoplasia Congenita Critical Region on the X Chromosome, Gene 1)," *Mol. Endocrinol.*, (2003), 17, 994-1004.

Zhou et al., "PNRC: A Proline-Rich Nuclear Receptor Coregulatory Protein That Modulates Transcriptional Activation of Multiple Nuclear Receptors Including Orphan Receptors SF1 (Steroidogenic Factor 1) and ERRα 1 (Estrogen Related Receptor α-1)," *Mol. Endocrinol.*, (2000), 14(7), 986-998.

Pogenberg et al., "Characterization of the Interaction between Retinoic Acid Receptor/Retinoid X Receptor (RAR/RXR) Heterodimers and Transcriptional Coactivators through Structural and Fluorescence Anisotropy Studies," *J. Biol. Chem.*, (2005), vol. 280, No. 2, 1625-1633.

Waters et al., "Structural Diversity in p160/CREB-binding Protein Coactivator Complexes," *J. Biol. Chem.*, (2006), vol. 281, No. 21, 14787-14795.

Bennett et al., "Non-Steroidal LXR Agonists; An Emerging Therapeutic Strategy for the Treatment of Atherosclerosis," *Recent Patents on Cardiovascular Drug Discovery*, (2006), 1, 21-46.

Willy et al., "LXR, a nuclear receptor that defines a distinct retinoid response pathway," *Genes & Dev.*, (1995), 9(9), 1033-1045.

LXR LIGAND TESTING METHOD

CROSS-REFERENCE TO RELATED APPLICATIONS

This application is the United States national phase application of International Application PCT/US2006/024945 filed Jun. 26, 2006. This application claims the benefit of priority under 35 USC 119(e) for U.S. provisional application Ser. No. 60/694,806 filed Jun. 28, 2005.

BACKGROUND OF THE INVENTION

Description of the Related Art

Plasma triglycerides and LDL cholesterol are known to be risk factors for arteriosclerosis. Hyperlipidemia, in which blood concentrations of triglycerides and LDL cholesterol are elevated, is a disease that not only causes impairment of vascular endothelial cells, but also causes deposition of cholesterol on vascular walls.

Since ATP binding transporter A1 (ABCA1) has a function that removes cholesterol deposited on vascular walls, it is believed that increasing the expressed amount of ABCA1 would make it possible to prevent progression of or improve arteriosclerosis (Bodzioch, M. et al. Nat. Genet., 22, 347-351, 1999).

The nuclear receptor, Liver X receptor (LXR) controls transcription of the regulatory gene of cholesterol and lipid metabolism. Since LXR agonists have the ability of increasing expression of ABCA1, LXR agonists are expected to be useful as novel anti-arteriosclerotic agents.

LXR is known to have two isoforms consisting of LXRα and LXRβ. LXRα is highly expressed in the liver, intestine, fat cells and kidney, and only slightly expressed in the adrenal, muscle and hematopoietic cells. On the other hand, LXRβ is universally ubiquitously expressed.

When a pan-LXR agonist was administered to wild-type mice, LXRα-deficient mice or LXRβ-deficient mice, the pan-LXR agonist elevated plasma triglyceride levels in wild-type mice and LXRα-deficient mice, whereas the pan-LXR agonist did not affect plasma triglycerides levels. From these results, a process has been disclosed for acquiring LXRβ-selective agonists (US2003/0073614A1).

When a ligand binds to a nuclear receptor, the three-dimensional structure of the nuclear receptor is changed, and these conformational changes are known to occur in the binding between the nuclear receptor and transcription associating factor, namely a coactivator or co-repressor protein. The type of coactivator that binds to the nuclear receptor varies according to the type of cell and tissue. In addition, if the ligand that binds with the nuclear receptor differs, then the change in the three-dimensional structure of the nuclear receptor also differs, and as a result, the types and numbers of coactivators that bind with the nuclear receptor also differ.

Although known examples of coactivator proteins for LXR include PGC-1α (Homo sapiens peroxisome proliferative activated receptor, gamma, coactivator 1, alpha: Proc Natl Acad Sci USA. 100, 5419-24, 2003), TIF-2(Homo sapiens nuclear receptor coactivator 2) (EMBO J., 23, 2083-2091, 2004), ASC-2 (Activating signal cointegrator 2) (Mol. Cell Biol., 23, 3583-3592, 2003), SRC-1 (Human steroid receptor coactivator-1) (Arterioscler Thromb. Vasc. Biol., 24, 703-708, 2004), DAX1 (dosage-sensitive sex reversal, adrenal hypoplasia congenital (AHC) critical region on the X chromosome, gene 1) (Mol. Endocrinol., 17, 994-1004, 2003), PNRC (proline-rich nuclear receptor coregulatory protein) (Mol. Endocrinol., 14, 986-998, 2000), TRAP220 (thyroid hormone receptor-associated protein 220) (J. Biol. Chem., 280, 1625-1633, 2005), PERC (Peroxisome proliferator-activated receptor gamma coactivator-1 beta) (J. Biol. Chem., 281, 14537-14546, 2006), ACTR (steroid receptor coactivator-3) (J. Biol. Chem., 281, 14787-14795, 2006), research on LXR ligands has yet to be conducted in consideration of the interaction between these coactivators and LXR as well as LXR ligands.

SUMMARY OF THE INVENTION

An object of the present invention is to provide a method of identifying LXR ligands that do not cause an effect, e.g., increase, in LDL cholesterol and/or plasma triglyceride concentrations in a mammal.

Moreover, another object of the present invention is to provide a method of easily measuring the effects of LXR ligands on plasma lipids.

Moreover, another object of the present invention is to provide a kit that can be used to identify LXR ligands that do not cause an effect, e.g., increase, in LDL cholesterol concentration and/or plasma triglycerides in a mammal.

As a result of conducting extensive studies to solve the aforementioned problems, the inventors of the present invention found that among LXR agonists, certain LXR agonists have the function of increasing low density lipoprotein (LDL) cholesterol concentration, and that LXR ligands for which there is low binding activity between LXRα and a specific coactivator are not observed or only observed to slightly increase plasma triglyceride and/or LDL cholesterol concentrations.

The inventors of the present invention also discovered a method of easily measuring whether an LXR ligand has the function of increasing plasma triglyceride concentration and/or LDL cholesterol concentration by utilizing the binding activity between LXR and a coactivator.

Moreover, the inventors of the present invention discovered a method of identifying LXR ligands that do not have the function of effecting, e.g., increasing, plasma triglyceride concentration and/or LDL cholesterol concentration in a mammal by utilizing the binding activity between LXR and a coactivator, thereby leading to completion of the present invention.

The present invention provides a method for easily measuring whether or not an LXR ligand has the function of effecting, e.g., increasing, plasma triglyceride concentration and/or LDL cholesterol concentration in a mammal.

Moreover, the present invention provides a method for identifying LXR ligands that do not have the function of effecting, e.g., increasing, plasma triglyceride concentration and/or LDL cholesterol concentration in a mammal.

Moreover, the present invention provides a kit that can be used in a method for identifying LXR ligands that do not cause a significant effect, e.g., increase, in LDL cholesterol concentration and/or plasma triglyceride concentration in a mammal.

These inventions are as follows:
1) A method of identifying a therapeutic or preventive agent that affects LDL cholesterol and/or plasma triglyceride concentration in a mammal, the method comprising:
(i) providing a heterodimer comprising LXRα and RXRα;
(ii) contacting a test substance with the heterodimer in the presence of an LXR coactivator;
(iii) measuring the amount of coactivator bound to the heterodimer;

(iv) comparing the amount of the coactivator measured in step (iii) with the amount of the coactivator bound to the heterodimer in a control; and (v) correlating the difference between the amount of bound coactivator and the amount of bound coactivator in the control as indicative of the activity of the test substance to significantly affect, e.g., increase, LDL cholesterol and/or plasma triglyceride concentration in a mammal.

2) The method according to 1), wherein the method is to identify a therapeutic or preventive agent that does not cause an increase in LDL cholesterol and/or plasma in a mammal.

3) The method according to 1), wherein the test substance is an LXR ligand.

4) The method according to 1) wherein the therapeutic or preventive agent is employed to treat or prevent a disease selected from the group consisting of arteriosclerosis, atherosclerosis, hyperlipidemia, lipid related diseases, an inflammatory disease mediated by inflammatory cytokines, autoimmune diseases, cardiovascular disease, cerebrovascular disease, renal disease, diabetes mellitus, diabetic complications, obesity, nephritis, hepatitis, and alzheimer's disease.

5) The method according to 1), wherein the coactivator is selected from the group consisting of PGC-1α (homo sapiens peroxisome proliferative activated receptor, gamma coactivator 1, alpha), TIF-2 (homo sapiens nuclear receptor coactivator 2), ASC-2 (activating signal cointegrator 2), SRC-1 (human steroid receptor coactivator-1), DAX1 (dosage-sensitive sex reversal, adrenal hypoplasia congenital (AHC) critical region on the X chromosome, gene 1), PNRC (proline-rich nuclear receptor coregulatory protein), TRAP220 (thyroid hormone receptor-associated protein 220), PERC (peroxisome proliferator-activated receptor gamma coactivator-1 beta) and ACTR (steroid receptor coactivator-3).

6) The method according to 1), wherein the coactivator is a peptide having an amino acid sequence selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and variants thereof.

7) The method according to 1), wherein the LXRα is a human full-length LXRα polypeptide having the amino acid sequence of SEQ ID NO: 2 or a variant thereof which has at least 80% identity to SEQ ID NO: 2, or a fused protein containing said polypeptide.

8) The method according to 1), wherein the LXRα is a ligand binding site of human full-length LXRα having the amino acid sequence of amino acid nos. 164 to 447 of SEQ ID NO: 2 or a variant thereof which has at least 80% identity to amino acid nos. 164 to 447 of SEQ ID NO: 2, or a fused protein containing said polypeptide.

9) The method according to 1), wherein the RXRα is a human full-length RXRα polypeptide having the amino acid sequence of SEQ ID NO: 4 or a variant thereof which has at least 80% identity to SEQ ID NO: 4, or a fused protein containing said polypeptide.

10) The method according to 1), wherein the RXRα is a ligand binding site of human full-length RXRα having the amino acid sequence of amino acid nos. 201 to 462 of SEQ ID NO: 4 or a variant thereof which has at least 80% identity to amino acid nos. 201 to 462 of SEQ ID NO: 4, or a fused protein containing said polypeptide.

11) The method according to 1) wherein the amount of the coactivator bound to the heterodimer is measured using a FRET assay.

12) The method according to 1), wherein the LXRα and/or the RXRα is provided by using cells that express LXRα and/or RXRα.

13) The method according to 1), wherein the LXRα and/or the RXRα is provided by using cells that express LXRα and/or RXRα as an exogenous protein.

14) The method according to 1) wherein the LXRα and/or the RXRα is provide by using cells that express LXRα and/or RXRα as an endogenous protein.

15) A kit which is used for any one of 1) to 14), the kit comprising one or more of the components selected from the group consisting of [A] to [L] below:

[A] a human full-length LXRα polypeptide, a human full-length RXRα polypeptide, and a coactivator selected from the group consisting of PGC-1α (homo sapiens peroxisome proliferative activated receptor gamma coactivator 1, alpha), TIF-2 (homo sapiens nuclear receptor coactivator 2), ASC-2 (activating signal cointegrator 2), SRC-1 (human steroid receptor coactivator-1), DAX1 (dosage-sensitive sex reversal, adrenal hypoplasia congenital (AHC) critical region on the X chromosome, gene 1), PNRC (proline-rich nuclear receptor coregulatory protein), TRAP220 (thyroid hormone receptor-associated protein 220), PERC (peroxisome proliferator-activated receptor gamma coactivator-1 beta) and ACTR (steroid receptor coactivator-3), wherein the human full-length LXRα polypeptide has the amino acid sequence of SEQ ID NO: 2 or a variant thereof which has at least 80% identity to SEQ ID NO: 2, and the human full-length RXRα polypeptide has the amino acid sequence of SEQ ID NO: 4 or a variant thereof which has at least 80% identity to SEQ ID NO: 4;

[B] a ligand binding site of a polypeptide described in [A], and any one of the coactivators set forth in [A]; and wherein the ligand binding site of a human full-length LXRα polypeptide has the amino acid sequence of amino acid nos. 164 to 447 of SEQ ID NO: 2 or a variant thereof which has at least 80% identity to amino acid nos. 164 to 447 of SEQ ID NO: 2, and a ligand binding site of human full-length RXRα polypeptide has the amino acid sequence of amino acid nos. 201 to 462 of SEQ ID NO: 4 or a variant thereof which has at least 80% identity to amino acid nos. 201 to 462 of SEQ ID NO: 4;

[C] a fused polypeptide containing a ligand binding site set forth in [B], and any one of the coactivators set forth in [A];

[D] a polypeptide set forth in any one of [A] to [C], and a polypeptide having an amino acid sequence selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and variants thereof;

[E] a polynucleotide encoding a polypeptide described in [A], and any one of the coactivators set forth in [A];

[F] a polynucleotide encoding a polypeptide described in [B], and any one of the coactivators set forth in [A];

[G] a polynucleotide encoding a polypeptide described in [C], and any one of the coactivators set forth in [A];

[H] a polynucleotide set forth in any one of [E] to [G], and a polypeptide having an amino acid sequence selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and variants thereof;

[I] a recombinant vector containing a polynucleotide set forth in any one of [E] to [H], and any one of the coactivators set forth in [A];

[J] a recombinant vector set forth in [I] that is an expression vector, and any one of the coactivators set forth in [A];

[K] host cells transformed with a recombinant vector set forth in [I] or [J], and any one of the coactivators set forth in [A]; and

[L] host cells set forth in [K] that are mammalian cells, and any one of the coactivators set forth in [A];

16) A method of diagnosing a disease state in a mammal comprising (i) collecting a biological sample, e.g., blood, plasma, liver, intestine, fat, kidney, adrenal gland, muscle or cells of the hematopoetic system, from the mammal;

(ii) contacting the biological sample with a heterodimer comprising LXRα and RXRα and a test substance in the presence of an LXR coactivator;

(iii) repeating said contacting step (i) with a control sample;

(iv) measuring the amount of the coactivator bound to the heterodimer;

(v) comparing the amount of the coactivator bound to the heterodimer in the biological sample collected from the mammal and the bound coactivator to the heterodimer in the control sample; and (vi) determining whether the mammal is in a disease state, when the amount of the coactivator in the biological sample is greater than the amount of the coactivator bound to the heterodimer in the control, which is indicative of an increase in LDL cholesterol and/or plasma concentration levels in the mammal.

17) The method according to 16), wherein the disease state is selected from the group consisting of (a) arteriosclerosis, (b) atherosclerosis, (c) hyperlipidemia, (d) a lipid-related disease, (e) an inflammatory disease mediated by an inflammatory cytokine, (f) an autoimmune disease, (g) a cardiovascular disease, (h) a cerebrovascular disease, (i) a renal disease, (j) diabetes mellitus, (k) a diabetic complication, (l) obesity, (m) nephritis, (n) hepatitis, (o) a tumor, (p) Alzheimer's disease and (q) arteriosclerosis caused by one or more of the diseases (c) to (o).

18) The method according to 17), wherein the mammal is a human.

19) The method according to 18), wherein the biological sample is a blood sample.

20) The method according to 19), wherein the coactivator is an LXR coactivator.

21) The method according to 20), wherein the method according to claim 19, wherein the coactivator is selected from the group consisting of PGC-1α (homo-sapiens peroxisome proliferative activated receptor, gamma coactivator 1, alpha), TIF-2 (homo sapiens nuclear receptor coactivator 2), ASC-2 (activating signal cointegrator 2), SRC-1 (human steroid receptor coactivator-1), DAX1 (dosage-sensitive sex reversal, adrenal hypoplasia congenital (AHC) critical region on the X chromosome, gene 1), PNRC (praline-rich nuclear receptor coregulatory protein), TRAP220 (thyroid hormone receptor-associated protein 220), PERC (peroxisome proliferator-activated receptor gamma coactivator-1 beta) and ACTR (steroid receptor coactivator-3).

DETAILED DESCRIPTION OF THE PREFERRED EMBODIMENTS

1. Explanation of Terms

The term "affect plasma triglyceride concentration" as used herein is intended to mean the use of LXR ligand as a therapeutic or preventive agent in regulating/monitoring the LDL cholesterol and plasma triglyceride concentration levels in a mammal, thereby inhibiting, preventing, ameliorating or reducing the risk of occurrence of a metabolic disease condition, such as atherosclerosis or an atherosclerotic disease event.

In the present specification, the term "arteriosclerosis-related diseases" refers to diseases that are present with symptoms of arteriosclerosis during the course of the disease from the time of onset, or diseases caused by arteriosclerosis. In addition, in the present specification, arteriosclerosis-related diseases refer to diseases for which all or a portion of the symptoms are improved by suppressing exacerbation of arteriosclerosis symptoms, improving arteriosclerosis symptoms, curing arteriosclerosis symptoms, preventing the appearance of arteriosclerosis symptoms or treating the causative disease.

Examples of arteriosclerosis-related diseases include arteriosclerosis, atherosclerosis, hyperlipidemia, lipid-related diseases, inflammatory diseases mediated by inflammatory cytokines, autoimmune diseases, cardiovascular diseases, cerebrovascular diseases.

Arteriosclerosis caused by one or more diseases selected from hyperlipidemia, lipid-related diseases, inflammatory diseases mediated by inflammatory cytokines, autoimmune diseases, cardiovascular diseases, cerebrovascular diseases, renal diseases, diabetes mellitus, diabetic complications, obesity is also included in the arteriosclerosis-related diseases of the present invention.

2. LXR Ligands

Although examples of LXR ligands include the compounds indicated below, there are no particular limitations on such compounds provided they are LXR ligands. For example, substances identified as LXR ligands based on the function of promoting expression of ABCA1 mRNA, the amount of cholesterol effluxed, cholesterol efflux activity or by the method described in a co-transfection assay, for example (WO2003/106435, Test Example 3) can also be used as LXR ligands in the present invention.

Examples of LXR ligands include: Compound 12 described on page 55 of International Publication WO2000/054759 (N-(2,2,2-trifluoroethyl)-N-{4-[2,2,2-trifluoro-1-hydroxy-1-(trifluoromethyl)ethyl]phenyl}benzene sulfonamide), 3-chloro-4-(3-(2-propyl-3-trifluoromethyl-6-benz-[4,5]-isooxazoloxy)propylthio)phenylacetic acid described in Example 20 on page 70 of WO1997/028137, 1-(2-Methoxyethyl)-4-[(4-methoxyphenyl)amino]-3-phenyl-5-thioxo-1,5-dihydro-2H-pyrrol-2-one described on page 41 of International Publication WO2005/005416, 2-methyl-N-{5-[2,2,2-trifluoro-1-hydroxy-1-(trifluoromethyl)ethyl]-1,3-thiazol-2yl}propanamide described on page 37 of WO03/090869, 1-[(6-fluoro(2H,4H-benzo[e][1,3-dioxin-8-yl))methoxy]-2-nitrobenzene described on page 27 of WO02/46181, 1-[1-(4-cyclohexylbenzoyl)-4-phenylpiperidin-4-yl]ethanone described on page 20 of WO2004/076418, 2-(3-{3-[[2-Chloro-3-(trifluoromethyl)benzyl](2,2-diphenylethyl) amino]propoxy}-phenyl)acetic acid described on page 46 of WO02/24632, methyl-4-amino-1-(2-chloro-6-fluorobenzyl)-2-piperidin-1-yl-1H-imidazole-5-carboxylate described on page 59 of WO2004/009091, 2,4-dihydroxy-3-propyl-1',1',1'-trifluoroacetophenone described on page 24 of WO03/045382, 3-chloro-4-(3-(3-ethyl-7-propyl-6-benz-[4,5]-isoxazoloxy)propylthio)phenylacetic acid described on page 42 of WO97/28137, 3-[({2-[(2,2-dimethylpropanoyl)thio]methyl}-N-(4-methoxylbenzyl)benzamide described on page 24 of WO2004/026816, N-(2-{[6-chloro-1,3-benzodioxol-5-yl]methyl}thiophenyl)-2-2-2-trifluoroacetamide described on page 29 of WO03/059874, 2-(3-{3-[(2-Chloro-3-(trifluoromethyl)-benzyl)-(2,2-diphenyl)-amino]-propoxy}phenyl)-1-morpholin-4-yl-ethanone hydrochloride salt described on page 45 of WO2004/043939, (R)-2-(3-{3-[[Chloro-3-(trifluoromethyl)benzyl](2,2-diphenylethyl)amino]-2-methyl-propoxy}-phenyl)acetic acid hydroxychloride salt described on page 43 of WO03/082802, 2-(3-{3-[[2-Chloro-3-(trifluoromethyl)benzyl](2,2-diphenyethyl)amino]propoxy}-phenyl)acetic acid, N-oxide described on page 55 of WO03/082205, N-(4-{1-Hydroxy-1-[1-(2-methoxyethyl)-1H-pyrrol-2-yl]-ethyl}-phenyl)-N-methyl-benzenesulfonamide described on page 33 of WO03/063796, N-Methyl-N-[2-methyl-4-(2,2,2-trifluoro-1-hydroxy-1-phenethyl)]-benzenesulfonamide described on page 29 of WO03/063576, [4-({3-[3-Benzyl-8-(trifluoromethyl)quinolin-4-yl]phenoxy}methyl)phenyl]acetic acid described on page 86 of WO05/058834, [4-({3-[2-Methyl-7-(trifluoromethyl)-2H-indazol-3-yl)phenoxy)methyl)phenyl]acetic acid described on page 251 of WO06/017384.

Examples of LXR ligands also include compounds having structure (1) to (165) shown in "Recent Patents on Cardiovascular Drug Discovery, 2006, 1, 21-46."

3. Preparation of LXRα, LXRβ and RXRα

Human LXRα, LXRβ and RXRα are not limited to their full-length proteins, but rather may also be partial peptides comprising of their partial sequences provided they contain the ligand binding domain. A human full-length LXRα has an amino acid sequence of SEQ ID NO: 2 or a variant thereof which has the ligand binding ability. A human full-length RXRα has an amino acid sequence of SEQ ID NO: 4 or a variant thereof which has the ligand binding ability. A human full-length LXRβ has an amino acid sequence of SEQ ID NO: 6 or a variant thereof which has the ligand binding ability. Suitably the degree of identity of polypeptide variants to SEQ ID NO: 2 or 4 or 6 is at least 80%, at least 90% or at least 95% or 100%. The degree of identity of a variant is preferably assessed by computer software, such as the BLAST program which uses an algorithm for performing homology searches. In addition, they may also be naturally-occurring proteins acquired from human-derived cells, and may also be proteins acquired from gene-recombinant cells designed to express said protein by a gene that has been cloned by PCR and so forth. In addition, these proteins may be purified or only partially purified.

Moreover, fused proteins, in which other amino acid sequences have been added to human LXRα, human LXRβ and human RXRα or their partial peptides, are also included in human LXRα, human LXRβ, human RXRα and their partial peptides. Examples of fused proteins include, but are not limited to, histidine tag fused proteins, FLAG fused proteins, and GFP and other fluorescent fused proteins.

Human LXRα gene is registered in GenBank as Accession No. U22662 (see P. J. Willy et al., Genes Dev. 9 (9), 1033-1045, 1995, nucleotide numbers 597 to 1379).

Human LXRβ gene is registered in GenBank as Accession No. U07132 (see P. J. Willy et al., Genes Dev. 9 (9), 1033-1045, 1995).

Human RXRα gene is registered in GenBank as Accession No. X52773.

4. Preparation of the Coactivator

Examples of LXR coactivators include PGC-1α (Homo sapiens peroxisome proliferative activated receptor, gamma, coactivator 1, alpha), TIF-2 (homo sapiens nuclear receptor coactivator 2), ASC-2 (activating signal cointegrator 2), SRC-1 (human steroid receptor coactivator-1), DAX1 (dosage-sensitive sex reversal, adrenal hypoplasia congenital (AHC) critical region on the X chromosome, gene 1), PNRC (proline-rich nuclear receptor coregulatory protein), TRAP220 (thyroid hormone receptor-associated protein 220), PERC (peroxisome proliferator-activated receptor gamma coactivator-1 beta), ACTR (steroid receptor coactivator-3). Coactivators are not limited to full-length proteins, but rather partial peptides containing an LXXLL motif (where L represents leucine and X represents an arbitrary amino acid) can also be used. The peptide selected from the group having an amino acid sequence of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and variants thereof which contain an LXXLL motif can also be used as a coactivator. Suitably the degree of identity of polypeptide variants to SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, or SEQ ID NO: 28 is at least 80%, at least 90% or at least 95% or 100%. These proteins may also be naturally-occurring proteins acquired from human-derived cells, and may also be proteins acquired from gene-recombinant cells designed to express said protein by a gene that has been cloned by PCR and so forth. In addition, chemically synthesized proteins may be used.

The nucleotide sequence of PGC-1α is registered in GenBank as Accession No. NM_013261. The nucleotide sequence of TIF-2 is registered in GenBank as Accession No. NM_006540. The nucleotide sequence of ASC-2 is registered in GenBank as Accession No. AF177388. The nucleotide sequence of SRC-1 is registered in GenBank as Accession No. U90661. The nucleotide sequence of DAX1 is registered in GenBank as Accession No. NP_000466. The nucleotide sequence of PNRC is registered in GenBank as Accession No. NM_000044. The nucleotide sequence of TRAP220 is registered in GenBank as Accession No. NM_004774. The nucleotide sequence of PERC is registered in GenBank as Accession No. NM_133263. The nucleotide sequence of ACTR is registered in GenBank as Accession No. AF012108.

5. Method of Assessing Function of Increasing LDL Cholesterol and/or Plasma Triglyceride Levels by LXR Ligands Whether or not an LXR ligand has the function of increasing plasma LDL cholesterol and/or plasma triglyceride concentrations can be assessed by whether or not said LXR ligand increases the amount of binding between LXRα and at least one coactivator selected from PGC-1α TIF-2, ASC-2, SRC-1, DAX1, PNRC, TRAP220, PERC and ACTR. More specifically, this method contains the steps of 1) or 2) below:

1)
i) a step of contacting a heterodimer comprising of LXRα and RXRα with an LXR coactivator and a test substance;
ii) a step of measuring the amount of coactivator bound to the heterodimer; and,
iii) a step of comparing the amount of coactivator measured in step ii) with the amount of coactivator bound to the heterodimer measured in the case of not contacting the heterodimer with the test substance.

2)
i) a step of contacting a heterodimer comprising of LXRα and RXRα with an LXR coactivator and a test substance;
ii) a step of measuring the amount of coactivator bound to the heterodimer;
iii) a step of comparing the amount of coactivator measured in step ii) with the amount of coactivator bound to the heterodimer measured in the case of not contacting the heterodimer with the test substance; and,
iv) a step of judging the LXR ligand to have the function of increasing plasma LDL cholesterol concentration and/or plasma triglyceride concentration in the case the amount of coactivator measured in step ii) increases in comparison with the amount of coactivator bound to the heterodimer measured in the case of not contacting the heterodimer with the test substance.

The following provides an explanation of each step.

1)
Step 1)-i):

A heterodimer comprising of LXRα and RXRα can be obtained by mixing LXRα and RXRα acquired according to the method described in the aforementioned section entitled "3. Preparation of LXRα, LXRβ and RXRα".

In addition, a heterodimer of LXRα and RXRα can be acquired by, for example, producing a vector that co-expresses a fused protein of the ligand binding domain (amino acid nos. 164 to 447 of SEQ ID NO: 2 of the Sequence Listing) of human LXRα (SEQ ID NO: 2) and His tag, and a fused protein of the ligand binding domain (amino acid nos. 201 to 462 of SEQ ID NO: 4 of the Sequence Listing) of RXRα (SEQ ID NO: 4) and FLAG, and purifying the protein expressed by a recombinant transformed with said expression vector.

Furthermore, a heterodimer comprising of LXRβ and RXRα used for a comparative experiment can be acquired by, for example, producing a vector that co-expresses a fused protein of the ligand binding domain (amino acid nos. 155 to 461 of SEQ ID NO: 6 of the Sequence Listing) of human LXRβ (SEQ ID NO: 6) and His tag, and a fused protein of the ligand binding domain (amino acid nos. 201 to 462 of SEQ ID NO: 4 of the Sequence Listing) of RXRα (SEQ ID NO: 4) and FLAG, and purifying the protein expressed by a recombinant transformed with said expression vector.

The LXR coactivators explained in the section entitled "4. Preparation of Coactivator" can be used for the LXR coactivator.

The substances described in the section entitled "2. LXR Ligands" can be used for the test substance.

In addition, a buffer for controlling the pH, or antibody for detecting the fused protein can be added to the reaction solution as necessary.

These materials are then mixed and subjected to the reaction, for example, described below.

Temperature conditions: 0° C. to 40° C., and preferably 4° C.

Reaction solution pH: 6 to 9, and preferably 7.4

Reaction time: 1 minute to 48 hours, and preferably 17 hours

The reaction can be carried out using, for example, a 384-well assay plate.

Step 1)-ii):

An example of a method for measuring the amount of coactivator bound to the heterodimer is described below.

In the case of carrying out the reaction in an assay plate using a coactivator in which the N-terminal has been biotinylated, the plate is subjected to excitation light at 337 nm with a fluorescent plate reader following completion of the reaction, the fluorescent intensity (A) at 665 nm and the fluorescent intensity (B) at 620 nm are determined, and the measured value at 655 nm is divided by the measured value at 620 nm followed by multiplying the resulting value by 1000 to determine the (C).

$$C=(A/B)\times 1000$$

A: Fluorescent intensity at 665 nm
B: Fluorescent intensity at 620 nm

Step 1)-iii):

The above value of (C) is divided by the value (C') obtained in the same experiment except for not adding the test substance, and that value is multiplied by 100 to determine the relative activity with respect to the control (R: % of control). The calculation formula is as shown below.

$$C'=(A'/B')\times 1000$$

$$R=C/C'\times 100$$

A': Fluorescent intensity at 665 nm in the case of carrying out the reaction without adding the test substance
B': Fluorescent intensity at 620 nm in the case of carrying out the reaction without adding the test substance This means that the higher the relative activity (R), the greater the bound amount of coactivator as compared with the control to which LXR ligand is not added.

In the case relative activity (R) is greater than 100, it can be judged that the amount of coactivator increases as a result of contacting the heterodimer with the test substance. A test substance can be judged to have less of a function that increases LDL cholesterol concentration and/or plasma triglyceride concentration the closer its value of relative activity is to 100.

In the case the relative activity of a test substance is higher than the relative activity determined for an LXR ligand for which the function of increasing LDL cholesterol and/or plasma triglyceride concentration is being investigated (referred to as "Compound X"), the function of increasing LDL cholesterol and/or plasma triglyceride concentration of the test substance can be judged to be stronger than that of Compound X.

In the case the relative activity of a test substance is lower than the relative activity determined for Compound X, the function of increasing LDL cholesterol and/or plasma triglyceride concentration of the test substance can be judged to be weaker than that of Compound X.

If the relative activities determined for a plurality of test substances are compared, a test substance can be judged to have a weaker function of increasing LDL cholesterol and/or plasma triglyceride concentration the lower its relative activity.

2)
Steps 2)-i), 2)-ii) and 2)-iii) are the same as the aforementioned steps 1)-i), 1)-ii) and 1)-iii).

Step 2)-iv):

As was explained in the aforementioned 1)-iii), a test substance can be judged to be a substance having less function that increases LDL cholesterol and/or plasma triglyceride concentration the closer its value of relative activity is to 100. Conversely, in the case its relative activity is greater than 100, the test substance can be judged to have a function that increases LDL cholesterol and/or plasma triglyceride concentration.

In the case the relative activity of a test substance is higher than the relative activity determined for an LXR ligand for which the function of increasing LDL cholesterol and/or plasma triglyceride concentration is being investigated (referred to as "Compound X"), the function of increasing LDL cholesterol and/or plasma triglyceride concentration of the test substance can be judged to be stronger than that of Compound X.

In the case the relative activity of a test substance is lower than the relative activity determined for Compound X, the function of increasing LDL cholesterol and/or plasma triglyceride concentration of the test substance can be judged to be weaker than that of Compound X.

If the relative activities determined for a plurality of test substances are compared, a test substance can be judged to have a weaker function of increasing LDL cholesterol and/or plasma triglyceride concentration the lower its relative activity.

In addition, in the aforementioned 1) and 2), in addition to being based on relative activity with respect to a single coactivator, relative activity can also be comprehensively assessed for a plurality of coactivators to judge the function of increasing plasma LDL cholesterol and/or plasma triglyceride concentration of a test substance.

6. Method for Identifying Substances Having Little or No Function of Increasing LDL Cholesterol and/or Plasma Triglyceride Concentration of an LXR Ligand The following steps make it possible to acquire an LXR ligand having little or no function of increasing LDL cholesterol and/or plasma triglyceride concentration:

i) a step of contacting a heterodimer comprising of LXRα and RXRα with an LXR coactivator and a test substance;
ii) a step of measuring the amount of coactivator bound to the heterodimer;
iii) a step of comparing the amount of coactivator measured in step ii) with the amount of coactivator bound to the heterodimer measured in the case of not contacting the heterodimer with the test substance; and,
iv) a step of judging the LXR ligand to have the function of increasing plasma LDL concentration and/or plasma triglyceride concentration in the case the amount of coactivator measured in step ii) does not increase in comparison with the amount of coactivator bound to the heterodimer measured in the case of not contacting the heterodimer with the test substance.

These steps can be carried out by the same method as the method described in the aforementioned section entitled "5. Method of Assessing Function of Increasing LDL Cholesterol and/or Plasma Triglyceride Levels by LXR Ligands".

The phrase "the amount of coactivator measured in step ii) does not increase" refers to at least one of the following conditions: a) relative activity is about 100, b) relative activity is demonstrated that is roughly equal to or less than the relative activity determined for an LXR ligand which is known to have little or no effect of increasing plasma LDL cholesterol and/or plasma triglyceride concentration.

According to this method, a substance identified to have little or no function of increasing LDL cholesterol and/or plasma triglyceride concentration can be a therapeutic or preventive agent of one or more of the diseases selected from the diseases of (a) to (q) indicated below.
(a) arteriosclerosis;
(b) atherosclerosis;
(c) hyperlipidemia;
(d) lipid-related diseases;
(e) inflammatory diseases mediated by inflammatory cytokines;
(f) autoimmune diseases;
(g) cardiovascular diseases;
(h) cerebrovascular diseases;
(i) renal diseases;
(j) diabetes mellitus;
(k) diabetic complications;
(l) obesity;
(m) nephritis;
(n) hepatitis;
(o) tumor;
(p) Alzheimer's disease; and
(q) arteriosclerosis caused by one or more of the diseases selected from (c) to (o).

7. A Kit for Identifying LXR Ligands

The kit indicated below can be used to identify LXR ligands that do not increase LDL cholesterol and/or plasma triglyceride concentration in a mammal, which comprises one or more of the components selected from the group consisting of [A] to [L] below:

[A] a human full-length LXRα polypeptide, a human full-length RXRα polypeptide, and a coactivator selected from the group consisting of PGC-1α (homo sapiens peroxisome proliferative activated receptor, gamma coactivator 1, alpha), TIF-2 (homo sapiens nuclear receptor coactivator 2), ASC-2 (activating signal cointegrator 2), SCR-1 (human steroid receptor coactivator-1), DAX1 (dosage-sensitive sex reversal, adrenal hypoplasia congenital (AHC) critical region on the X chromosome, gene 1), PNRC (proline-rich nuclear receptor coregulatory protein), TRAP220 (thyroid hormone receptor-associated protein 220), PERC (peroxisome proliferator-activated receptor gamma coactivator-1 beta) and ACTR (steroid receptor coactivator-3),
wherein the human full-length LXRα polypeptide has the amino acid sequence of SEQ ID NO: 2 or a variant thereof which has at least 80% identity to SEQ ID NO: 2, and the human full-length RXRα polypeptide has at least 80% identity to SEQ ID NO: 4;
[B] a ligand binding site of a polypeptide described in [A], and any one of the coactivators set forth in [A], wherein the ligand binding site of a human full-length LXRα polypeptide has the amino acid sequence of amino acid nos. 164 to 447 of SEQ ID NO: 2 or a variant thereof which has at least 80% identity to amino acid nos. 164 to 447 of SEQ ID NO: 2, and a ligand binding site of human full-length RXRα polypeptide has the amino acid sequence of amino acid nos. 201 to 462 of SEQ ID NO: 4 or a variant thereof which has at least 80% identity to amino acid nos. 201 to 462 of SEQ ID NO: 4;
[C] a fused polypeptide containing a ligand binding site set forth in [B], and any one of the coactivators set forth in [A];
[D] a polypeptide set forth in any one of [A] to [C], and a polypeptide having an amino acid sequence selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID No: 28 and variants thereof;
[E] a polynucleotide encoding a polypeptide described in [A], and any one of the coactivators set forth in [A];
[F] a polynucleotide encoding a polypeptide described in [B], and any one of the coactivators set forth in [A];
[G] a polynucleotide encoding a polypeptide described in [C], and any one of the coactivators set forth in [A];
[H] a polynucleotide set forth in any one of [E] to [G], and a polypeptide having an amino acid sequence selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and variants thereof;
[I] a recombinant vector containing a polynucleotide set forth in any one of [E] to [H], and any one of the coactivators set forth in [A];
[J] a recombinant vector set forth in [I] that is an expression vector, and any one of the coactivators set forth in [A];
[K] host cells transformed with a recombinant vector set forth in [I] or [J], and any one of the coactivators set forth in [A]; and
[L] host cells set forth in [K] that are mammalian cells, and any one of the coactivators set forth in [A].

EXAMPLES

Although the following provides a more detailed explanation of the present invention through its test examples and examples, the present invention is not limited thereto.

Test Example 1

Measurement of LXR Ligand Cholesterol Efflux Activity (Cholesterol Efflux Assay)

The cholesterol efflux activity of two types of LXR ligands (Compound A (N-(2,2,2-trifluoroethyl)-N-{4-[2,2,2-trifluoro-1-hydroxy-1-(trifluoromethyl)ethyl]phenyl}benzenesulfonamide and Compound B (3-chloro-4-(3-(2-propyl-3-trifluoromethyl-6-benz-[4,5]-isoxazoloxy)propylthio)phenylacetic acid) was measured using the method described below.

$3 \times 10^5$ THP-1 cells (ATCC No.: TIB-202) were disseminated in a 96-well white plate (Costar) followed by the addition of 200 nM Phorbol 12-Myristate 13-Acetate (Sigma) and culturing for 24 hours at 37° C. in a $CO_2$ incubator.

Next, 125 µl aliquots of medium (RPMI 1640 (Invitrogen)+1% fetal bovine serum (hereinafter referred to as "FBS", (Invitrogen)) containing 0.2 µCi/ml 4-$^{14}$C-Cholesterol (Perkin-Elmer) were added to each well followed by additionally culturing for 48 hours at 37° C. in a $CO_2$ incubator.

Following completion of culturing, 100 µl of PBS containing 0.2% bovine serum albumin (hereinafter referred to as "BSA", (Sigma Chemical)) were added to each well to wash the cells. Next, 100 µl of RPMI 1640 containing Apolipoprotein A1 (hereinafter referred to as "ApoA1", (Biogenesis)) at a final concentration of 10 µg/ml, or RPMI 1640 not containing ApoA1, were added to each well. Next, a DMSO solution was added to the wells so that the final concentration of Compound A (N-(2,2,2-trifluoroethyl)-N-{4-[2,2,2-trifluoro-1-hydroxy-1-(trifluoromethyl)ethyl]phenyl}benzenesulfonamide or Compound B (3-chloro-4-(3-(2-propyl-3-trifluoromethyl-6-benz-[4,5]-isoxazoloxy)propylthio)phenylacetic acid) was 0.01 µM, 0.1 µM and 1 µM each and the final concentration of DMSO was 1%, followed by culturing for 24 hours at 37° C. in a $CO_2$ incubator.

Following completion of culturing, the plate was centrifuged for 5 minutes at 1,000 rpm and 4° C. 75 µl of medium in the form of the centrifuged supernatant were transferred to a 96-well Luma plate (Packard) and allowed to dry. On the other hand, 100 µl of PBS were added to each well of the plate in which the cells had settled to wash the cells.

250 µl aliquots of Micro Scinti 20 (Packard) were added to each well of the plate containing the washed cells and allowed to stand overnight, followed by measuring the radioactivity of the medium and cells with a scintillation counter (Top Count, Packard). Percent (%) efflux was calculated from the measured values using the calculation formula shown below.

% efflux=(Specific radioactivity of medium(*CPM*)/ 75×100)/(Specific radioactivity of medium (*CPM*)+specific radioactivity of cells(*CPM*))× 100

The value of % efflux obtained from Compound A at a concentration of 1 µM was assigned a value of 100, and the other results were converted on the basis of this value to determine relative activity (Table 1). Compound A and Compound B demonstrated cholesterol efflux activity of about 50% at a final concentration of 0.01 µM, demonstrated efflux activity of about 100% at 1 µM, and LXR ligands in the form of Compound A and Compound B were clearly determined to have equal cholesterol efflux activity.

TABLE 1

| Compound final concentration | 0.01 µM | 0.1 µM | 1 µM |
|---|---|---|---|
| Compound A | 49% | 86% | 100% |
| Compound B | 54% | 90% | 101% |

Example 1

Acquisition of Histidine Tag Fused Proteins (1) Construction of Expression Plasmid of Histidine Tag Fused Human LXRα Protein Oligonucleotides comprising of the following nucleotide sequences:

gccatatgcgggaggagtgtgtcctgtc (LXRα-F: SEQ ID NO: 7 of the Sequence Listing), ctggatccttcgtgcacatcccagatct (LXRα-R: SEQ ID NO: 8 of the Sequence Listing)

were synthesized with a DNA synthesizer for use as PCR primers, PCR was carried out by using as template a human liver cDNA library (see P. J. Willy et al., Genes Dev. 9 (9), 1033-1045 (1995)), and a DNA fragment was amplified in which restriction enzyme NdeI and BamHI sites were introduced at the ligand binding domain (hereinafter referred to as "LBD": amino acid nos. 164 to 447 of SEQ ID NO: 2 of Sequence Listing) of human LXRα (SEQ ID NO: 2). The DNA fragment was digested with restriction enzyme NdeI and BamHI, and ligated to His tag fused protein expression plasmid pET15b (Novagen) digested with NdeI and BamHI. The resulting Histidine tag fused human LXRα protein expression plasmid was designated as pET15b-LXRα.

(2) Construction of Expression Plasmid of Histidine Tag Fused Human LXRβ Protein Oligonucleotides comprising of the following nucleotide sequences:

gccatatgagggagcagtgcgtcctttc (LXRβ-F: SEQ ID NO: 9 of the Sequence Listing)

ctggatccctcgtggacgtcccagatct (LXRβ-R: SEQ ID NO: 10 of the Sequence Listing)

were used as PCR primers, PCR was carried out by using as template a human liver cDNA library, and a DNA fragment was amplified in which restriction enzyme NdeI and BamHI sites were introduced at the ligand binding domain (LBD: amino acid nos. 155 to 461 of SEQ ID NO: 6) of human LXRβ (SEQ ID NO: 6). The amplified DNA fragment was digested with restrictases NdeI and BamHI, and ligated to His tag fused protein expression plasmid pET15b (Novagen) digested with NdeI and BamHI. The resulting histidine tag fused human LXRβ protein expression plasmid was designated as pET15b-LXRβ.

(3) Construction of His-LXRα, FLAG-RXRα Co-Expression Plasmid and His-LXRβ, FLAG-RXRα Co-Expression Plasmid Oligonucleotides comprising of the following nucleotide sequences:

ccagatctaagcgggaagccgtgcagga (RXRα-F: SEQ ID NO: 11 of the Sequence Listing)

ccagatcagtcatttggtgcggcgcct (RXR-R: SEQ ID NO: 12 of the Sequence Listing)

were used as PCR primers, PCR was carried out by using as template human liver cDNA (Clontech), and a DNA fragment was amplified in which a BglII site was introduced at the ligand binding domain (amino acid nos. 201 to 462 of SEQ ID NO: 4) of human RXRα (GenBank Accession No. X52773; SEQ ID NO: 4). The amplified DNA fragment was digested with restriction enzyme BglII, and ligated to pET15b-LXRα digested with BamHI to construct a plasmid that co-expresses His-LXRα (SEQ ID NO: 13) and FLAG-RXRα (SEQ ID NO: 14 of the Sequence Listing) designated as pET15b-LXRα/FLAG-RXRα.

In addition, the aforementioned DNA fragment obtained by PCR was digested with BglII and incorporated at the BamHI site of pET15b-LXRβ digested with BamHI to construct a plasmid that co-expresses His-LXRβ (SEQ ID NO: 15) and FLAG-RXRα designated as pET15b-LXRβ/FLAG-RXRα.

(4) Acquisition of His-LXRα/FLAG-RXRα and His-LXRβ/FLAG-RXRα

*Escherichia coli* strain BL21(DE3) was transformed using pET15b-LXRα/FLAG-RXRα or pET15b-LXRβ/FLAG-RXRα. Each of the resulting transformants were shake cultured for 4 hours at 37° C. in 20 ml of L-broth medium (containing 10 g of tryptone (Difco), 5 g of yeast extract (Difco), 5 g of sodium chloride each in a 1 L aqueous solution) containing 100 μg/ml of ampicillin. Next, the transformants were inoculated at 5.0% (v/v) into 400 ml of L-broth medium containing 100 μg/ml of ampicillin and shake cultured for 4 hours at 37° C. Subsequently, 0.1 mM isopropyl-β-D-thiogalactopyranoside (hereinafter referred to as "IPTG") was added followed by shaking culture for 17 hours at 25° C.

Following completion of the reaction, the microbial cells were collected by centrifugal separation for 10 minutes at 8,000×g, and then suspended in 40 ml of lysis buffer (Table 2). Subsequently, the cells were disrupted by a ultrasonic homogenizer, and after removing the insoluble fraction by centrifugal separation (11,000×g, 20 minutes), 2 ml of $Ni^{2+}$ resin (Probond Resin, Invitrogen) were added followed by shaking gently for 1.5 hours on ice. After washing the gel seven times with 20 ml of wash buffer (Table 3), the gel was eluted four times using 1 ml of elution buffer (Table 4) according to the batch method to obtain 4 ml each of His-LXRα/FLAG-RXRα and His-LXRβ/FLAG-RXRα. After carrying out 12.5% SDS polyacrylamide gel electrophoresis (hereinafter referred to as "SDS-PAGE"), the purified proteins were confirmed to be present at the locations corresponding to the predicted molecular weights of the fused protein of 35,500 for His-LXRα, 37,200 for His-LXRβ and 30,900 for FLAG-RXRα, and the protein concentrations were determined according to the Bradford method. 4 ml of storage solution (Table 5) was added to the resulting protein solutions after which they were stored at −20° C.

TABLE 2

| Lysis buffer (pH 8.0) | |
| --- | --- |
| $NaH_2PO_4$ | 50 mM |
| NaCl | 300 mM |
| $MgCl_2$ | 5 mM |
| Tween 20 | 0.05% (v/v) |
| Glycerol | 10% (v/v) |
| Imidazole | 10 mM |

TABLE 3

| Wash buffer (pH 8.0) | |
| --- | --- |
| $NaH_2PO_4$ | 50 mM |
| NaCl | 300 mM |
| $MgCl_2$ | 5 mM |
| Tween 20 | 0.05% (v/v) |
| Glycerol | 10% (v/v) |
| Imidazole | 20 mM |

TABLE 4

| Elution buffer (pH 8.0) | |
| --- | --- |
| $NaH_2PO_4$ | 50 mM |
| NaCl | 300 mM |
| $MgCl_2$ | 5 mM |
| Tween 20 | 0.05% (v/v) |
| Glycerol | 10% (v/v) |
| Imidazole | 250 mM |

TABLE 5

| Srorage solution | |
| --- | --- |
| Glycerol | 90% (v/v) |
| EDTA | 2 mM |
| (±)-Dithiothreitol | 20 mM |
| PMSF | 2 mM |
| β-Mercaptoethanol | 10 mM |
| Protease inhibitor | |

Example 2

Selection of LXR Ligands Based on the Binding Capacity to LXRα Using Fluorescence Resonance Energy Transfer (Hereinafter Referred to as "FRET") Assay 8 μl of LXRα reaction solution (0.05 μl of 4 μM His-LXRα and FLAG-RXRα mixed solution, 1.00 μl of 10×PBS (Sigma Chemical), 2.50 μl of 2 M KF (Wako Pure Chemical Industries), 0.10 μl of 10% NP40 (Sigma Chemical), 0.15 μl of anti-His tag antibody (CIS Bio International) and 4.20 μl of $H_2O$) containing the His-LXRα and FLAG-RXRα prepared according to Example 1 were placed in a 384-well assay plate (Greiner Bio-One).

Next, 2 μl of a solution of Compound A (N-(2,2,2-trifluoroethyl)-N-{4-[2,2,2-trifluoro-1-hydroxy-1-(trifluoromethyl)ethyl]phenyl}benzene sulfonamide (Compound 12 described on page 55 of International Publication WO2000/054759) or Compound B (3-chloro-4-(3-(2-propyl-3-trifluoromethyl-6-benz-[4,5]-isooxazoloxy)propylthio)phenylacetic acid (a compound described in Example 20 on page 70 of International Publication WO1997/028137), dissolved to a concentration of 10 μM in dimethyl sulfoxide (hereinafter referred to as "DMSO"), were added to each well of a 384-well assay plate followed by incubating for 1 hour at room temperature.

Next, 10 μl of peptide reaction solution (1.00 μl of 5 μM peptide, 1.00 μl of 10×PBS, 2.50 μl of 2 M KF, 0.10 μl of 10% NP40, 0.20 μl of streptavidin (CIS Bio International) and 5.20 μl of $H_2O$) were added to each well of the 384-well assay plate and incubated for 17 hours at 4° C. The peptide added here was comprising of any of the amino acid sequences of (a) to (g) below, and the amino acid of the N-terminal was biotinylated.

(a) PGC-1α: DGTPPPQEAEEPSLLKKLLLAPANT (aa 130-154) (NM_013261) (SEQ ID NO: 16 of the Sequence Listing)
(b) TIF2: HGTSLKEKHKILHRLLQDSSSPVDL (aa 679-703)(NM_006540) (SEQ ID NO: 17 of the Sequence Listing)
(c) ASC-2 NR-1: NKDVTLTSPLLVNLLQSDISAGHFGVNNKQ (LXXLL motif on the N-terminal side of ASC-2) (aa 887-906) (AF177388)(SEQ ID NO: 18 of the Sequence Listing)
(d) ASC-2 NR-2: SPAMREAPTSLSQLLDNSGAPNVTIKPPGL (LXXLL motif on the C-terminal side of ASC-2) (aa 1481-1510) (SEQ ID NO: 19 of the Sequence Listing)
(e) SRC-1-2: CPSSHSSLTERHKILHRLLQEGSPS (the second LXXLL motif from the N-terminal side of SRC-1) (aa 676-700) (U90661) (SEQ ID NO: 20 of the Sequence Listing)
(f) SRC-1-3: KESKDHQLLRYLLDKDEKDL (the third LXXLL motif from the N-terminal side of SRC-1) (aa 741-760) (SEQ ID NO: 21 of the Sequence Listing)
(g) SRC-1-4: QKPTSGPQTPQAQQKSLLQQLLTE (the fourth LXXLL motif from the N-terminal side of SRC-1) (aa 1418-1441)(SEQ ID NO: 22 of the Sequence Listing)

Following completion of incubation, the assay plate was subjected to excitation light at 337 nm using a fluorescent plate reader (Envision, Perkin-Elmer), and fluorescent absorbance at 665 nm and 620 nm was measured to determine the binding capacity between the protein and the peptide.

The value obtained by multiplying 1000 by the value resulting from dividing the measured value at 665 nm when applying excitation light at 337 nm by the measured value at 620 nm was determined. This value was then divided by the value determined by the same method when only DMSO was added without adding LXR ligand (Compound A or Compound B), and this value was then multiplied by 100 and indicated as the percentage relative to the control (% of control) as shown in Table 6.

The value for % of control determined here is the value, represented by a percentage, that indicates the ratio of the increase in the amount of coactivator bound to LXRα that results from adding LXR ligand, and the larger this value, the larger the amount of coactivator that binds to LXRα.

According to the present Example, Compound A was identified as a compound that increases the amount of coactivator bound to LXRα, while Compound B was identified as a compound that does not increase the amount bound.

Although Compound A and Compound B demonstrated equal cholesterol efflux activity based on the results of Test Example 1, the amount of coactivator bound to LXRα was greater for Compound A than Compound B.

Example 3

Selection of LXR Ligands Based on Binding Capacity to LXRβ Using Fluorescence Resonance Energy Transfer (Hereinafter Referred to as "FRET") Assay (1)

8 μl of LXRβ reaction solution (0.025 μl of 8 μM His-LXRβ and FLAG-RXRα mixed solution, 1.00 μl of 10×PBS, 2.50 μl of 2 M KF, 0.10 μl of 10% NP40, 0.15 μl of anti-His tag antibody and 4.23 μl of H$_2$O) containing the His-LXRβ and FLAG-RXRα prepared according to Example 1 were placed in a 384-well assay plate (Greiner Bio-One) and measured according to the same method as Example 2 to determine the % of control (Table 6). There was no significant difference observed in the resulting values between Compound A and Compound B.

TABLE 6

| Peptide | LXRα (% of control) | | LXRβ (% of control) | |
|---|---|---|---|---|
| | Compound A | Compound B | Compound A | Compound B |
| PGC-1α | 361.7 | 207.1 | 191.0 | 195.0 |
| ASC2 NR-1 | 155.8 | 116.0 | 114.5 | 115.1 |
| ASC2 NR-2 | 254.0 | 137.2 | 120.4 | 116.3 |
| SRC1-2 | 267.0 | 182.1 | 120.4 | 119.4 |
| SRC1-3 | 181.3 | 111.6 | 110.6 | 108.4 |
| SRC1-4 | 207.3 | 128.3 | 154.6 | 143.9 |
| TIF2 | 266.7 | 157.1 | 107.9 | 114.4 |

Example 4

Selection of LXR Ligands Based on the Binding Capacity to LXRα and LXRβ Using Fluorescence Resonance Energy Transfer (Hereinafter Referred to as "FRET") Assay (1) According to the same method as Example 2) (using the following peptides (h) to (m), instead of the peptides (a) to (g) in Example 2), the amount of coactivator bound to the heterodimer LXRα and RXRα were determined.

The amount of the coactivator bound to the heterodimer comprising LXRα and RXRα was greater for Compound A than for Compound B (Table 7).

(h) DAX1: CCFCGEDHPRQGSILYSLLTSSKQT (aa 132-156) (NP_000466) (SEQ ID NO: 23 of the Sequence Listing)
(i) PNRC: KNPTSCSRRFYQLTKLLDSVQPIAR (aa 848-872) (NM_000044) (SEQ ID NO: 24 of the Sequence Listing)
(j) TIF2 NRB2: KQEPVSPKKKENALLRYLLDKDDTK (aa 731-755) (NM_006540) (SEQ ID NO: 25 of the Sequence Listing)
(k) TRAP220: GHGEDFSKVSQNPILTSLLQITGNG (aa 590-614) (NM_004774) (SEQ ID NO: 26 of the Sequence Listing)
(l) PERC NRB2: HSKASWAEFSILRELLAQDVLCD (aa 332-354) (NM_133263) (SEQ ID NO: 27 of the Sequence Listing)
(m) ACTR NRB3: SPKKKENNALLRYLLDRDDPSDALSK (aa 728-753) (AF012108) (SEQ ID NO: 28 of the Sequence Listing)

(2) LXR5: According to the same method in Example 3) (using the above peptides (h) to (m), instead of peptides (a) to (g) in Example 3), the amount of the coactivator bound to the heterodimer comprising LXRβ and RXRα were determined. There was no significant difference observed in the resulting values between Compound A and Compound B (Table 7).

TABLE 7

| Peptide | LXRα (% of control) | | LXRβ (% of control) | |
|---|---|---|---|---|
| | Compound A | Compound B | Compound A | Compound B |
| DAX1 | 158 | 107 | 116 | 120 |
| PNRC | 140 | 110 | 109 | 107 |
| TIF2 NRB2 | 268 | 127 | 125 | 124 |
| TRAP220 | 131 | 107 | 111 | 116 |
| PERC NRB2 | 127 | 104 | 104 | 115 |
| ACTR NRB3 | 167 | 92 | 129 | 103 |

Test Example 2

Cynomolgus Monkey Consecutive Daily Administration Study

Five to seven year old, male cynomolgus monkeys in groups of 5 animals each were force fed only an administration base (Propylene glycol (Wako Pure Chemical Industries)/Tween 80 (Kao) (volume ratio: 4/1, hereinafter referred to as "PG/Tween")) (hereinafter referred to as "the control group"), or Compound A or Compound B dissolved in PG/Tween in an amount of 3 mg/kg or 10 mg/kg once a day for 7 days between the hours of 8:00 and 10:00 AM. After fasting for 16 hours starting at 5:00 PM on the 7th day of administration, 1 mL of blood was collected from the cephalic vein with a heparinized syringe followed by centrifuging for 15 minutes at 4° C. and 5000 rpm to obtain plasma.

The levels of LDL cholesterol and triglycerides in the plasma were measured with an auto analyzer (Hitachi Model 7170) followed by calculation of the % of control group (Tables 8 and 9).

Compound A, which was identified in Example 2 as being a compound that increases the amount of coactivator bound to LXRα, was clearly determined to increase LDL cholesterol concentration and triglyceride concentration in the plasma as compared with a compound identified as a compound that does not increase the amount of coactivator bound to LXRα.

Namely, whether or not an LXR ligand has the function of increasing plasma LDL cholesterol concentration and triglyceride concentration was clearly determined to be able to be assessed simply by measuring the amount of coactivator bound to a heteroprotein of LXRα and RXRα at the time of addition of LXR ligand without having to conduct an animal study.

TABLE 8

Relative value of LDL Cholesterol in Plasma

| | Daily Dosage of Compound | |
|---|---|---|
| | 3 mg/kg | 10 mg/kg |
| Compound A | 137% | 207% |
| Compound B | 111% | 150% |

TABLE 9

Relative value of TG in Plasma

| | Daily Dosage of Compound | |
|---|---|---|
| | 3 mg/kg | 10 mg/kg |
| Compound A | 429% | 661% |
| Compound B | 73% | 120% |

---

What is claimed is:

1. A method of identifying a therapeutic or preventive agent that affects LDL cholesterol concentration and/or plasma triglyceride concentration in a mammal, the method comprising:
   (i) providing a heterodimer comprising LXRα and RXRα;
   (ii) contacting a test substance with the heterodimer in the presence of an LXR coactivator;
   (iii) measuring the amount of the coactivator bound to the heterodimer;
   (iv) comparing the amount of the coactivator measured in step (iii) with the amount of the coactivator bound to the heterodimer in a control;
   (v) correlating the difference between the amount of bound coactivator and the amount of bound coactivator in the control as indicative of the activity of the test substance to affect the LDL cholesterol concentration and/or the plasma triglyceride concentration in a mammal;
   wherein the activity of the test substance to affect the LDL cholesterol concentration and/or the plasma triglyceride concentration is greater when the amount of the coactivator bound to the heterodimer is higher than the amount of the coactivator bound to the heterodimer in the control.

2. The method according to claim 1, wherein the method is to identify a therapeutic or preventive agent that does not cause an increase in LDL cholesterol and/or plasma triglyceride concentration in a mammal.

3. The method according to claim 1, wherein the test substance is a LXR ligand.

4. The method according to claim 1, wherein the therapeutic or preventive agent is to treat or prevent a disease selected from the group consisting of arteriosclerosis, atherosclerosis, hyperlipidemia, lipid related diseases, inflammatory disease mediated by inflammatory cytokines, autoimmune diseases, cardiovascular disease, cerebrovascular disease, renal disease, diabetes mellitus, diabetic complications, obesity, nephritis, hepatitis and alzheimer's disease.

5. The method according to claim 1, wherein the coactivator is selected from the group consisting of PGC-1α (homo sapiens peroxisome proliferative activated receptor, gamma coactivator 1, alpha), TIF-2 (homo sapiens nuclear receptor coactivator 2), ASC-2 (activating signal cointegrator 2), SRC-1 (human steroid receptor coactivator-1), DAX1 (dosage-sensitive sex reversal, adrenal hypoplasia congenital (AHC) critical region on the X chromosome, gene 1), PNRC (proline-rich nuclear receptor coregulatory protein), TRAP220 (thyroid hormone receptor-associated protein 220), PERC (peroxisome proliferator-activated receptor gamma coactivator-1 beta) and ACTR (steroid receptor coactivator-3).

6. The method according to claim 1, wherein the coactivator is a peptide having an amino acid sequence selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and variants thereof.

7. The method according to claim 1, wherein the LXRα is a human full-length LXRα polypeptide having an amino acid sequence of SEQ ID NO: 2 or a variant thereof which has at least 80% identity to SEQ ID NO: 2, or a fused protein containing said polypeptide.

8. The method according to claim 1, wherein the LXRα is a ligand binding site of human full-length LXRα having an amino acid sequence of amino acid nos. 164 to 447 of SEQ ID NO: 2 or a variant thereof which has at least 80% identity to amino acid nos. 164 to 447 of SEQ ID NO: 2, or a fused protein containing said polypeptide.

9. The method according to claim 1, wherein the RXRα is a human full-length RXRα polypeptide having an amino acid sequence of SEQ ID NO: 4 or a variant thereof which has at least 80% identity to SEQ ID NO: 4, or a fused protein containing said polypeptide.

10. The method according to claim 1, wherein the RXRα is a ligand binding site of human full-length RXRα having an amino acid sequence of amino acid nos. 201 to 462 of SEQ ID NO: 4 or a variant thereof which has at least 80% identity to amino acid nos. 201 to 462 of SEQ ID NO: 4, or a fused protein containing said polypeptide.

11. The method according to claim 1, wherein the amount of the coactivator bound to the heterodimer is measured using a FRET assay.

12. The method according to claim 1, wherein the LXRα and/or the RXRα is provided by using cells that express LXRα and/or RXRα.

13. The method according to claim 1, wherein the LXRα and/or the RXRα is provided by using cells that express LXRα and/or RXRα as an exogenous protein.

14. The method according to claim 1, wherein the LXRα and/or the RXRα is provided by using cells that express LXRα and/or RXRα as an endogenous protein.

* * * * *

SEQUENCE LISTING

```
<160> NUMBER OF SEQ ID NOS: 28

<210> SEQ ID NO 1
<211> LENGTH: 1528
<212> TYPE: DNA
<213> ORGANISM: Homo sapiens
<220> FEATURE:
<221> NAME/KEY: CDS
<222> LOCATION: (36)..(1379)

<400> SEQUENCE: 1
cagtgccttg gtaatgacca gggctccaga aagag atg tcc ttg tgg ctg ggg          53
                                      Met Ser Leu Trp Leu Gly
                                       1               5 gcc cct gtg cct gac att cct cct gac tct gcg gtg gag ctg tgg aag       101
Ala Pro Val Pro Asp Ile Pro Pro Asp Ser Ala Val Glu Leu Trp Lys
             10                  15                  20 cca ggc gca cag gat gca agc agc cag gcc cag gga ggc agc agc tgc       149
Pro Gly Ala Gln Asp Ala Ser Ser Gln Ala Gln Gly Gly Ser Ser Cys
         25                  30                  35 atc ctc aga gag gaa gcc agg atg ccc cac tct gct ggg ggt act gca       197
Ile Leu Arg Glu Glu Ala Arg Met Pro His Ser Ala Gly Gly Thr Ala
     40                  45                  50 ggg gtg ggg ctg gag gct gca gag ccc aca gcc ctc ctc acc agg gca       245
Gly Val Gly Leu Glu Ala Ala Glu Pro Thr Ala Leu Leu Thr Arg Ala
 55                  60                  65                  70 gag ccc cct tca gaa ccc aca gag atc cgt cca caa aag cgg aaa aag       293
Glu Pro Pro Ser Glu Pro Thr Glu Ile Arg Pro Gln Lys Arg Lys Lys
                 75                  80                  85 ggg cca gcc ccc aaa atg ctg ggg aac gag cta tgc agc gtg tgt ggg       341
Gly Pro Ala Pro Lys Met Leu Gly Asn Glu Leu Cys Ser Val Cys Gly
             90                  95                 100 gac aag gcc tcg ggc ttc cac tac aat gtt ctg agc tgc gag ggc tgc       389
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Asp | Lys | Ala | Ser | Gly | Phe | His | Tyr | Asn | Val | Leu | Ser | Cys | Glu | Gly | Cys  |
|     | 105 |     |     |     | 110 |     |     |     |     | 115 |     |     |     |     |      |

```
aag gga ttc ttc cgc cgc agc gtc atc aag gga gcg cac tac atc tgc         437
Lys Gly Phe Phe Arg Arg Ser Val Ile Lys Gly Ala His Tyr Ile Cys
    120             125                 130 cac agt ggc ggc cac tgc ccc atg gac acc tac atg cgt cgc aag tgc         485
His Ser Gly Gly His Cys Pro Met Asp Thr Tyr Met Arg Arg Lys Cys
135             140                 145                 150 cag gag tgt cgg ctt cgc aaa tgc cgt cag gct ggc atg cgg gag gag         533
Gln Glu Cys Arg Leu Arg Lys Cys Arg Gln Ala Gly Met Arg Glu Glu
                155                 160                 165 tgt gtc ctg tca gaa gaa cag atc cgc ctg aag aaa ctg aag cgg caa         581
Cys Val Leu Ser Glu Glu Gln Ile Arg Leu Lys Lys Leu Lys Arg Gln
        170                 175                 180 gag gag gaa cag gct cat gcc aca tcc ttg ccc ccc agg cgt tcc tca         629
Glu Glu Glu Gln Ala His Ala Thr Ser Leu Pro Pro Arg Arg Ser Ser
            185                 190                 195 ccc ccc caa atc ctg ccc cag ctc agc ccg gaa caa ctg ggc atg atc         677
Pro Pro Gln Ile Leu Pro Gln Leu Ser Pro Glu Gln Leu Gly Met Ile
        200                 205                 210 gag aag ctc gtc gct gcc cag caa cag tgt aac cgg cgc tcc ttt tct         725
Glu Lys Leu Val Ala Ala Gln Gln Gln Cys Asn Arg Arg Ser Phe Ser
215                 220                 225                 230 gac cgg ctt cga gtc acg cct tgg ccc atg gca cca gat ccc cat agc         773
Asp Arg Leu Arg Val Thr Pro Trp Pro Met Ala Pro Asp Pro His Ser
                235                 240                 245 cgg gag gcc cgt cag cag cgc ttt gcc cac ttc act gag ctg gcc atc         821
Arg Glu Ala Arg Gln Gln Arg Phe Ala His Phe Thr Glu Leu Ala Ile
            250                 255                 260 gtc tct gtg cag gag ata gtt gac ttt gct aaa cag cta ccc ggc ttc         869
Val Ser Val Gln Glu Ile Val Asp Phe Ala Lys Gln Leu Pro Gly Phe
        265                 270                 275 ctg cag ctc agc cgg gag gac cag att gcc ctg ctg aag acc tct gcg         917
Leu Gln Leu Ser Arg Glu Asp Gln Ile Ala Leu Leu Lys Thr Ser Ala
    280                 285                 290 atc gag gtg atg ctt ctg gag aca tct cgg agg tac aac cct ggg agt         965
Ile Glu Val Met Leu Leu Glu Thr Ser Arg Arg Tyr Asn Pro Gly Ser
295                 300                 305                 310 gag agt atc acc ttc ctc aag gat ttc agt tat aac cgg gaa gac ttt        1013
Glu Ser Ile Thr Phe Leu Lys Asp Phe Ser Tyr Asn Arg Glu Asp Phe
                315                 320                 325 gcc aaa gca ggg ctg caa gtg gaa ttc atc aac ccc atc ttc gag ttc        1061
Ala Lys Ala Gly Leu Gln Val Glu Phe Ile Asn Pro Ile Phe Glu Phe
            330                 335                 340 tcc agg gcc atg aat gag ctg caa ctc aat gat gcc gag ttt gcc ttg        1109
Ser Arg Ala Met Asn Glu Leu Gln Leu Asn Asp Ala Glu Phe Ala Leu
        345                 350                 355 ctc att gct atc agc atc ttc tct gca gac cgg ccc aac gtg cag gac        1157
Leu Ile Ala Ile Ser Ile Phe Ser Ala Asp Arg Pro Asn Val Gln Asp
    360                 365                 370 cag ctc cag gtg gag agg ctg cag cac aca tat gtg gaa gcc ctg cat        1205
Gln Leu Gln Val Glu Arg Leu Gln His Thr Tyr Val Glu Ala Leu His
375                 380                 385                 390 gcc tac gtc tcc atc cac cat ccc cat gac cga ctg atg ttc cca cgg        1253
Ala Tyr Val Ser Ile His His Pro His Asp Arg Leu Met Phe Pro Arg
                395                 400                 405 atg cta atg aaa ctg gtg agc ctc cgg acc ctg agc agc gtc cac tca        1301
Met Leu Met Lys Leu Val Ser Leu Arg Thr Leu Ser Ser Val His Ser
            410                 415                 420 gag caa gtg ttt gca ctg cgt ctg cag gac aaa aag ctc cca ccg ctg        1349
```

-continued

```
Glu Gln Val Phe Ala Leu Arg Leu Gln Asp Lys Lys Leu Pro Pro Leu
            425                 430                 435 ctc tct gag atc tgg gat gtg cac gaa tga ctgttctgtc ccatatttt         1399
Leu Ser Glu Ile Trp Asp Val His Glu
        440                 445 ctgttttctt ggccggatgg ctgaggcctg gtggctgcct cctagaagtg gaacagactg    1459
agaagggcaa acattcctgg gagctgggca aggagatcct cccgtggcat taaaagagag    1519
tcaaagggt                                                            1528

<210> SEQ ID NO 2
<211> LENGTH: 447
<212> TYPE: PRT
<213> ORGANISM: Homo sapiens

<400> SEQUENCE: 2

Met Ser Leu Trp Leu Gly Ala Pro Val Pro Asp Ile Pro Pro Asp Ser
1               5                   10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
    50                  55                  60

Ala Leu Leu Thr Arg Ala Glu Pro Pro Ser Glu Pro Thr Glu Ile Arg
65                  70                  75                  80

Pro Gln Lys Arg Lys Gly Pro Ala Pro Lys Met Leu Gly Asn Glu
                85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Arg Ser Ser Pro Pro Gln Ile Leu Pro Gln Leu Ser Pro
        195                 200                 205

Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Pro Trp Pro Met
225                 230                 235                 240

Ala Pro Asp Pro His Ser Arg Glu Ala Arg Gln Gln Arg Phe Ala His
                245                 250                 255

Phe Thr Glu Leu Ala Ile Val Ser Val Gln Glu Ile Val Asp Phe Ala
            260                 265                 270

Lys Gln Leu Pro Gly Phe Leu Gln Leu Ser Arg Glu Asp Gln Ile Ala
        275                 280                 285

Leu Leu Lys Thr Ser Ala Ile Glu Val Met Leu Leu Glu Thr Ser Arg
    290                 295                 300

Arg Tyr Asn Pro Gly Ser Glu Ser Ile Thr Phe Leu Lys Asp Phe Ser
305                 310                 315                 320
```

```
Tyr Asn Arg Glu Asp Phe Ala Lys Ala Gly Leu Gln Val Glu Phe Ile
            325                 330                 335

Asn Pro Ile Phe Glu Phe Ser Arg Ala Met Asn Glu Leu Gln Leu Asn
            340                 345                 350

Asp Ala Glu Phe Ala Leu Leu Ile Ala Ile Ser Ile Phe Ser Ala Asp
            355                 360                 365

Arg Pro Asn Val Gln Asp Gln Leu Gln Val Glu Arg Leu Gln His Thr
370                 375                 380

Tyr Val Glu Ala Leu His Ala Tyr Val Ser Ile His His Pro His Asp
385                 390                 395                 400

Arg Leu Met Phe Pro Arg Met Leu Met Lys Leu Val Ser Leu Arg Thr
            405                 410                 415

Leu Ser Ser Val His Ser Glu Gln Val Phe Ala Leu Arg Leu Gln Asp
            420                 425                 430

Lys Lys Leu Pro Pro Leu Leu Ser Glu Ile Trp Asp Val His Glu
            435                 440                 445

<210> SEQ ID NO 3
<211> LENGTH: 1866
<212> TYPE: DNA
<213> ORGANISM: Homo sapiens
<220> FEATURE:
<221> NAME/KEY: CDS
<222> LOCATION: (76)..(1464)

<400> SEQUENCE: 3
gaattccggc gccgggggcc gcccgcccgc cgcccgctgc ctgcgccgcc ggccgggcat      60
gagttagtcg cagac atg gac acc aaa cat ttc ctg ccg ctc gat ttc tcc     111
                 Met Asp Thr Lys His Phe Leu Pro Leu Asp Phe Ser
                  1               5                  10 acc cag gtg aac tcc tcc ctc acc tcc ccg acg ggg cga ggc tcc atg     159
Thr Gln Val Asn Ser Ser Leu Thr Ser Pro Thr Gly Arg Gly Ser Met
           15                  20                  25 gct gcc ccc tcg ctg cac ccg tcc ctg ggg cct ggc atc ggc tcc ccg     207
Ala Ala Pro Ser Leu His Pro Ser Leu Gly Pro Gly Ile Gly Ser Pro
       30                  35                  40 gga cag ctg cat tct ccc atc agc acc ctg agc tcc ccc atc aac ggc     255
Gly Gln Leu His Ser Pro Ile Ser Thr Leu Ser Ser Pro Ile Asn Gly
45                  50                  55                  60 atg ggc ccg cct ttc tcg gtc atc agc tcc ccc atg ggc ccc cac tcc     303
Met Gly Pro Pro Phe Ser Val Ile Ser Ser Pro Met Gly Pro His Ser
                65                  70                  75 atg tcg gtg ccc acc aca ccc acc ctg ggc ttc agc act ggc agc ccc     351
Met Ser Val Pro Thr Thr Pro Thr Leu Gly Phe Ser Thr Gly Ser Pro
            80                  85                  90 cag ctc agc tca cct atg aac ccc gtc agc agc agc gag gac atc aag     399
Gln Leu Ser Ser Pro Met Asn Pro Val Ser Ser Ser Glu Asp Ile Lys
        95                 100                 105 ccc ccc ctg ggc ctc aat ggc gtc ctc aag gtc ccc gcc cac ccc tca     447
Pro Pro Leu Gly Leu Asn Gly Val Leu Lys Val Pro Ala His Pro Ser
    110                 115                 120 gga aac atg gct tcc ttc acc aag cac atc tgc gcc atc tgc ggg gac     495
Gly Asn Met Ala Ser Phe Thr Lys His Ile Cys Ala Ile Cys Gly Asp
125                 130                 135                 140 cgc tcc tca ggc aag cac tat gga gtg tac agc tgc gag ggg tgc aag     543
Arg Ser Ser Gly Lys His Tyr Gly Val Tyr Ser Cys Glu Gly Cys Lys
                145                 150                 155 ggc ttc ttc aag cgg acg gtg cgc aag gac ctg acc tac acc tgc cgc     591
Gly Phe Phe Lys Arg Thr Val Arg Lys Asp Leu Thr Tyr Thr Cys Arg
```

```
              160              165               170
gac aac aag gac tgc ctg att gac aag cgg cag cgg aac cgg tgc cag    639
Asp Asn Lys Asp Cys Leu Ile Asp Lys Arg Gln Arg Asn Arg Cys Gln
        175                 180                 185 tac tgc cgc tac cag aag tgc ctg gcc atg ggc atg aag cgg gaa gcc    687
Tyr Cys Arg Tyr Gln Lys Cys Leu Ala Met Gly Met Lys Arg Glu Ala
        190                 195                 200 gtg cag gag gag cgg cag cgt ggc aag gac cgg aac gag aat gag gtg    735
Val Gln Glu Glu Arg Gln Arg Gly Lys Asp Arg Asn Glu Asn Glu Val
205                 210                 215                 220 gag tcg acc agc agc gcc aac gag gac atg ccg gtg gag agg atc ctg    783
Glu Ser Thr Ser Ser Ala Asn Glu Asp Met Pro Val Glu Arg Ile Leu
                225                 230                 235 gag gct gag ctg gcc gtg gag ccc aag acc gag acc tac gtg gag gca    831
Glu Ala Glu Leu Ala Val Glu Pro Lys Thr Glu Thr Tyr Val Glu Ala
            240                 245                 250 aac atg ggg ctg aac ccc agc tcg ccg aac gac cct gtc acc aac att    879
Asn Met Gly Leu Asn Pro Ser Ser Pro Asn Asp Pro Val Thr Asn Ile
        255                 260                 265 tgc caa gca gcc gac aaa cag ctt ttc acc ctg gtg gag tgg gcc aag    927
Cys Gln Ala Ala Asp Lys Gln Leu Phe Thr Leu Val Glu Trp Ala Lys
270                 275                 280 cgg atc cca cac ttc tca gag ctg ccc ctg gac gac cag gtc atc ctg    975
Arg Ile Pro His Phe Ser Glu Leu Pro Leu Asp Asp Gln Val Ile Leu
285                 290                 295                 300 ctg cgg gca ggc tgg aat gag ctg ctc atc gcc tcc ttc tcc cac cgc   1023
Leu Arg Ala Gly Trp Asn Glu Leu Leu Ile Ala Ser Phe Ser His Arg
                305                 310                 315 tcc atc gcc gtg aag gac ggg atc ctc ctg gcc acc ggg ctg cac gtc   1071
Ser Ile Ala Val Lys Asp Gly Ile Leu Leu Ala Thr Gly Leu His Val
            320                 325                 330 cac cgg aac agc gcc cac agc gca ggg gtg ggc gcc atc ttt gac agg   1119
His Arg Asn Ser Ala His Ser Ala Gly Val Gly Ala Ile Phe Asp Arg
        335                 340                 345 gtg ctg acg gag ctt gtg tcc aag atg cgg gac atg cag atg gac aag   1167
Val Leu Thr Glu Leu Val Ser Lys Met Arg Asp Met Gln Met Asp Lys
350                 355                 360 acg gag ctg ggc tgc ctg cgc gcc atc gtc ctc ttt aac cct gac tcc   1215
Thr Glu Leu Gly Cys Leu Arg Ala Ile Val Leu Phe Asn Pro Asp Ser
365                 370                 375                 380 aag ggg ctc tcg aac ccg gcc gag gtg gag gcg ctg agg gag aag gtc   1263
Lys Gly Leu Ser Asn Pro Ala Glu Val Glu Ala Leu Arg Glu Lys Val
                385                 390                 395 tat gcg tcc ttg gag gcc tac tgc aag cac aag tac cca gag cag ccg   1311
Tyr Ala Ser Leu Glu Ala Tyr Cys Lys His Lys Tyr Pro Glu Gln Pro
            400                 405                 410 gga agg ttc gct aag ctc ttg ctc cgc ctg ccg gct ctg cgc tcc atc   1359
Gly Arg Phe Ala Lys Leu Leu Leu Arg Leu Pro Ala Leu Arg Ser Ile
        415                 420                 425 ggg ctc aaa tgc ctg gaa cat ctc ttc ttc ttc aag ctc atc ggg gac   1407
Gly Leu Lys Cys Leu Glu His Leu Phe Phe Phe Lys Leu Ile Gly Asp
430                 435                 440 aca ccc att gac acc ttc ctt atg gag atg ctg gag gcg ccg cac caa   1455
Thr Pro Ile Asp Thr Phe Leu Met Glu Met Leu Glu Ala Pro His Gln
445                 450                 455                 460 atg act tag gcctgcgggc ccatcctttg tgcccacccg ttctggccac             1504
Met Thr cctgcctgga cgccagctgt tcttctcagc ctgagccctg tccctgccct tctctgcctg   1564
gcctgtttgg actttggggc acagcctgtc actgctctgc ctaagagatg tgttgtcacc   1624
```

-continued

```
ctccttattt ctgttactac ttgtctgtgg cccagggcag tggctttcct gagcagcagc    1684
cttcgtggca agaactagcg tgagcccagc caggcgcctc cccaccgggc tctcaggacg    1744
ccctgccaca cccacggggc ttgggcgact acagggtctt cggccccagc cctggagctg    1804
caggagttgg gaacggggct tttgtttccg ttgctgttta tcgatgctgg ttttcagaat    1864
tc                                                                   1866

<210> SEQ ID NO 4
<211> LENGTH: 462
<212> TYPE: PRT
<213> ORGANISM: Homo sapiens

<400> SEQUENCE: 4

Met Asp Thr Lys His Phe Leu Pro Leu Asp Phe Ser Thr Gln Val Asn
1               5                   10                  15

Ser Ser Leu Thr Ser Pro Thr Gly Arg Gly Ser Met Ala Ala Pro Ser
                20                  25                  30

Leu His Pro Ser Leu Gly Pro Gly Ile Gly Ser Pro Gly Gln Leu His
            35                  40                  45

Ser Pro Ile Ser Thr Leu Ser Ser Pro Ile Asn Gly Met Gly Pro Pro
        50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

Pro Met Asn Pro Val Ser Ser Glu Asp Ile Lys Pro Pro Leu Gly Leu
            100                 105                 110

Leu Asn Gly Val Leu Lys Val Pro Ala His Pro Ser Gly Asn Met Ala
            115                 120                 125

Ser Phe Thr Lys His Ile Cys Ala Ile Cys Gly Asp Arg Ser Ser Gly
        130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
        275                 280                 285

Phe Ser Glu Leu Pro Leu Asp Asp Gln Val Ile Leu Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
```

```
                      325                 330                 335
Ala His Ser Ala Gly Val Gly Ala Ile Phe Asp Arg Val Leu Thr Glu
                340                 345                 350

Leu Val Ser Lys Met Arg Asp Met Gln Met Asp Lys Thr Glu Leu Gly
            355                 360                 365

Cys Leu Arg Ala Ile Val Leu Phe Asn Pro Asp Ser Lys Gly Leu Ser
        370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
            420                 425                 430

Leu Glu His Leu Phe Phe Phe Lys Leu Ile Gly Asp Thr Pro Ile Asp
        435                 440                 445

Thr Phe Leu Met Glu Met Leu Glu Ala Pro His Gln Met Thr
    450                 455                 460

<210> SEQ ID NO 5
<211> LENGTH: 2010
<212> TYPE: DNA
<213> ORGANISM: Homo sapiens
<220> FEATURE:
<221> NAME/KEY: CDS
<222> LOCATION: (245)..(1630)

<400> SEQUENCE: 5
caagaagtgg cgaagttacc tttgagggta tttgagtagc ggcggtgtgt caggggctaa      60
agaggaggac gaagaaaagc agagcaaggg aacccagggc aacaggagta gttcactccg     120
cgagaggccg tccacgagac ccccgcgcgc aggcatgagc cccgcccccc acgcatgagc     180
cccgcccccc gctgttgctt ggagaggggc gggacctgga gagaggctgc tccgtgaccc     240 cacc atg tcc tct cct acc acg agt tcc ctg gat acc ccc ctg cct gga     289
     Met Ser Ser Pro Thr Thr Ser Ser Leu Asp Thr Pro Leu Pro Gly
     1               5                   10                  15 aat ggc ccc cct cag cct ggc gcc cct tct tct tca ccc act gta aag     337
Asn Gly Pro Pro Gln Pro Gly Ala Pro Ser Ser Ser Pro Thr Val Lys
                20                  25                  30 gag gag ggt ccg gag ccg tgg ccc ggg ggt ccg gac cct gat gtc cca     385
Glu Glu Gly Pro Glu Pro Trp Pro Gly Gly Pro Asp Pro Asp Val Pro
            35                  40                  45 ggc act gat gag gcc agc tca gcc tgc agc aca gac tgg gtc atc cca     433
Gly Thr Asp Glu Ala Ser Ser Ala Cys Ser Thr Asp Trp Val Ile Pro
        50                  55                  60 gat ccc gaa gag gaa cca gag cgc aag cga aag aag ggc cca gcc ccg     481
Asp Pro Glu Glu Glu Pro Glu Arg Lys Arg Lys Lys Gly Pro Ala Pro
    65                  70                  75 aag atg ctg ggc cac gag ctt tgc cgt gtc tgt ggg gac aag gcc tcc     529
Lys Met Leu Gly His Glu Leu Cys Arg Val Cys Gly Asp Lys Ala Ser
80                  85                  90                  95 ggc ttc cac tac aac gtg ctc agc tgc gaa ggc tgc aag ggc ttc ttc     577
Gly Phe His Tyr Asn Val Leu Ser Cys Glu Gly Cys Lys Gly Phe Phe
                100                 105                 110 cgg cgc agt gtg gtc cgt ggt ggg gcc agg cgc tat gcc tgc cgg ggt     625
Arg Arg Ser Val Val Arg Gly Gly Ala Arg Arg Tyr Ala Cys Arg Gly
            115                 120                 125 ggc gga acc tgc cag atg gac gct ttc atg cgg cgc aag tgc cag cag     673
Gly Gly Thr Cys Gln Met Asp Ala Phe Met Arg Arg Lys Cys Gln Gln
        130                 135                 140
```

| | | |
|---|---|---|
| tgc cgg ctg cgc aag tgc aag gag gca ggg atg agg gag cag tgc gtc<br>Cys Arg Leu Arg Lys Cys Lys Glu Ala Gly Met Arg Glu Gln Cys Val<br>145 150 155 | | 721 |
| ctt tct gaa gaa cag atc cgg aag aag aag att cgg aaa cag cag cag<br>Leu Ser Glu Glu Gln Ile Arg Lys Lys Lys Ile Arg Lys Gln Gln Gln<br>160 165 170 175 | | 769 |
| cag gag tca cag tca cag tcg cag tca cct gtg ggg ccg cag ggc agc<br>Gln Glu Ser Gln Ser Gln Ser Gln Ser Pro Val Gly Pro Gln Gly Ser<br>180 185 190 | | 817 |
| agc agc tca gcc tct ggg cct ggg gct tcc cct ggt gga tct gag gca<br>Ser Ser Ser Ala Ser Gly Pro Gly Ala Ser Pro Gly Gly Ser Glu Ala<br>195 200 205 | | 865 |
| ggc agc cag ggc tcc ggg gaa ggc gag ggt gtc cag cta aca gcg gct<br>Gly Ser Gln Gly Ser Gly Glu Gly Glu Gly Val Gln Leu Thr Ala Ala<br>210 215 220 | | 913 |
| caa gaa cta atg atc cag cag ttg gtg gcg gcc caa ctg cag tgc aac<br>Gln Glu Leu Met Ile Gln Gln Leu Val Ala Ala Gln Leu Gln Cys Asn<br>225 230 235 | | 961 |
| aaa cgc tcc ttc tcc gac cag ccc aaa gtc acg ccc tgg ccc ctg ggc<br>Lys Arg Ser Phe Ser Asp Gln Pro Lys Val Thr Pro Trp Pro Leu Gly<br>240 245 250 255 | | 1009 |
| gca gac ccc cag tcc cga gat gcc cgc cag caa cgc ttt gcc cac ttc<br>Ala Asp Pro Gln Ser Arg Asp Ala Arg Gln Gln Arg Phe Ala His Phe<br>260 265 270 | | 1057 |
| acg gag ctg gcc atc atc tca gtc cag gag atc gtg gac ttc gct aag<br>Thr Glu Leu Ala Ile Ile Ser Val Gln Glu Ile Val Asp Phe Ala Lys<br>275 280 285 | | 1105 |
| caa gtg cct ggt ttc ctg cag ctg ggc cgg gag gac cag atc gcc ctc<br>Gln Val Pro Gly Phe Leu Gln Leu Gly Arg Glu Asp Gln Ile Ala Leu<br>290 295 300 | | 1153 |
| ctg aag gca tcc act atc gag atc atg ctg cta gag aca gcc agg cgc<br>Leu Lys Ala Ser Thr Ile Glu Ile Met Leu Leu Glu Thr Ala Arg Arg<br>305 310 315 | | 1201 |
| tac aac cac gag aca gag tgt atc acc ttc ttg aag gac ttc acc tac<br>Tyr Asn His Glu Thr Glu Cys Ile Thr Phe Leu Lys Asp Phe Thr Tyr<br>320 325 330 335 | | 1249 |
| agc aag gac gac ttc cac cgt gca ggc ctg cag gtg gag ttc atc aac<br>Ser Lys Asp Asp Phe His Arg Ala Gly Leu Gln Val Glu Phe Ile Asn<br>340 345 350 | | 1297 |
| ccc atc ttc gag ttc tcg cgg gcc atg cgg cgg ctg ggc ctg gac gac<br>Pro Ile Phe Glu Phe Ser Arg Ala Met Arg Arg Leu Gly Leu Asp Asp<br>355 360 365 | | 1345 |
| gct gag tac gcc ctg ctc atc gcc atc aac atc ttc tcg gcc gac cgg<br>Ala Glu Tyr Ala Leu Leu Ile Ala Ile Asn Ile Phe Ser Ala Asp Arg<br>370 375 380 | | 1393 |
| ccc aac gtg cag gag ccg ggc cgc gtg gag gcg ttg cag cag ccc tac<br>Pro Asn Val Gln Glu Pro Gly Arg Val Glu Ala Leu Gln Gln Pro Tyr<br>385 390 395 | | 1441 |
| gtg gag gcg ctg ctg tcc tac acg cgc atc aag agg ccg cag gac cag<br>Val Glu Ala Leu Leu Ser Tyr Thr Arg Ile Lys Arg Pro Gln Asp Gln<br>400 405 410 415 | | 1489 |
| ctg cgc ttc ccg cgc atg ctc atg aag ctg gtg agc ctg cgc acg ctg<br>Leu Arg Phe Pro Arg Met Leu Met Lys Leu Val Ser Leu Arg Thr Leu<br>420 425 430 | | 1537 |
| agc tct gtg cac tcg gag cag gtc ttc gcc ttg cgg ctc cag gac aag<br>Ser Ser Val His Ser Glu Gln Val Phe Ala Leu Arg Leu Gln Asp Lys<br>435 440 445 | | 1585 |
| aag ctg ccg cct ctg ctg tcg gag atc tgg gac gtc cac gag tga<br>Lys Leu Pro Pro Leu Leu Ser Glu Ile Trp Asp Val His Glu<br>450 455 460 | | 1630 |

```
ggggctggcc acccagcccc acagccttgc ctgaccaccc tccagcagat agacgccggc    1690 acccttcct cttcctaggg tggaaggggc cctgggcgag cctgtagacc tatcggctct     1750
catcccttgg gataagcccc agtccaggtc caggaggctc cctccctgcc cagcgagtct    1810
tccagaaggg gtgaaagggt tgcaggtccc gaccactgac ccttcccggc tgccctccct    1870
ccccagctta cacctcaagc ccagcacgca gcgtaccttg aacagaggga ggggaggacc    1930
catggctctc ccccctagc ccgggagacc aggggccttc tcttcctct gcttttattt     1990 aataaaaata aaaacagaaa                                                2010
```

<210> SEQ ID NO 6
<211> LENGTH: 461
<212> TYPE: PRT
<213> ORGANISM: Homo sapiens

<400> SEQUENCE: 6

```
Met Ser Ser Pro Thr Thr Ser Ser Leu Asp Thr Pro Leu Pro Gly Asn
1               5                   10                  15

Gly Pro Pro Gln Pro Gly Ala Pro Ser Ser Pro Thr Val Lys Glu
            20                  25                  30

Glu Gly Pro Glu Pro Trp Pro Gly Gly Pro Asp Pro Asp Val Pro Gly
        35                  40                  45

Thr Asp Glu Ala Ser Ser Ala Cys Ser Thr Asp Trp Val Ile Pro Asp
    50                  55                  60

Pro Glu Glu Glu Pro Glu Arg Lys Arg Lys Lys Gly Pro Ala Pro Lys
65                  70                  75                  80

Met Leu Gly His Glu Leu Cys Arg Val Cys Gly Asp Lys Ala Ser Gly
                85                  90                  95

Phe His Tyr Asn Val Leu Ser Cys Glu Gly Cys Lys Gly Phe Phe Arg
            100                 105                 110

Arg Ser Val Val Arg Gly Gly Ala Arg Arg Tyr Ala Cys Arg Gly Gly
        115                 120                 125

Gly Thr Cys Gln Met Asp Ala Phe Met Arg Arg Lys Cys Gln Gln Cys
    130                 135                 140

Arg Leu Arg Lys Cys Lys Glu Ala Gly Met Arg Glu Gln Cys Val Leu
145                 150                 155                 160

Ser Glu Glu Gln Ile Arg Lys Lys Lys Ile Arg Lys Gln Gln Gln Gln
                165                 170                 175

Glu Ser Gln Ser Gln Ser Gln Ser Pro Val Gly Pro Gln Gly Ser Ser
            180                 185                 190

Ser Ser Ala Ser Gly Pro Gly Ala Ser Pro Gly Gly Ser Glu Ala Gly
        195                 200                 205

Ser Gln Gly Ser Gly Glu Gly Glu Gly Val Gln Leu Thr Ala Ala Gln
    210                 215                 220

Glu Leu Met Ile Gln Gln Leu Val Ala Ala Gln Leu Gln Cys Asn Lys
225                 230                 235                 240

Arg Ser Phe Ser Asp Gln Pro Lys Val Thr Pro Trp Pro Leu Gly Ala
                245                 250                 255

Asp Pro Gln Ser Arg Asp Ala Arg Gln Gln Arg Phe Ala His Phe Thr
            260                 265                 270

Glu Leu Ala Ile Ile Ser Val Gln Glu Ile Val Asp Phe Ala Lys Gln
        275                 280                 285

Val Pro Gly Phe Leu Gln Leu Gly Arg Glu Asp Gln Ile Ala Leu Leu
    290                 295                 300
```

```
Lys Ala Ser Thr Ile Glu Ile Met Leu Leu Glu Thr Ala Arg Arg Tyr
305                 310                 315                 320

Asn His Glu Thr Glu Cys Ile Thr Phe Leu Lys Asp Phe Thr Tyr Ser
                325                 330                 335

Lys Asp Asp Phe His Arg Ala Gly Leu Gln Val Glu Phe Ile Asn Pro
            340                 345                 350

Ile Phe Glu Phe Ser Arg Ala Met Arg Arg Leu Gly Leu Asp Asp Ala
        355                 360                 365

Glu Tyr Ala Leu Leu Ile Ala Ile Asn Ile Phe Ser Ala Asp Arg Pro
    370                 375                 380

Asn Val Gln Glu Pro Gly Arg Val Glu Ala Leu Gln Gln Pro Tyr Val
385                 390                 395                 400

Glu Ala Leu Leu Ser Tyr Thr Arg Ile Lys Arg Pro Gln Asp Gln Leu
                405                 410                 415

Arg Phe Pro Arg Met Leu Met Lys Leu Val Ser Leu Arg Thr Leu Ser
            420                 425                 430

Ser Val His Ser Glu Gln Val Phe Ala Leu Arg Leu Gln Asp Lys Lys
        435                 440                 445

Leu Pro Pro Leu Leu Ser Glu Ile Trp Asp Val His Glu
    450                 455                 460

<210> SEQ ID NO 7
<211> LENGTH: 28
<212> TYPE: DNA
<213> ORGANISM: Artificial Sequence
<220> FEATURE:
<223> OTHER INFORMATION: PCR forward primer for LXR-alpha ligand binding
      region

<400> SEQUENCE: 7
gccatatgcg ggaggagtgt gtcctgtc                                         28

<210> SEQ ID NO 8
<211> LENGTH: 28
<212> TYPE: DNA
<213> ORGANISM: Artificial Sequence
<220> FEATURE:
<223> OTHER INFORMATION: PCR reverse primer for LXR-alpha ligand binding
      region

<400> SEQUENCE: 8
ctggatcctt cgtgcacatc ccagatct                                         28

<210> SEQ ID NO 9
<211> LENGTH: 28
<212> TYPE: DNA
<213> ORGANISM: Artificial Sequence
<220> FEATURE:
<223> OTHER INFORMATION: PCR forward primer for LXR-beta ligand binding
      region

<400> SEQUENCE: 9
gccatatgag ggagcagtgc gtcctttc                                         28

<210> SEQ ID NO 10
<211> LENGTH: 28
<212> TYPE: DNA
<213> ORGANISM: Artificial Sequence
<220> FEATURE:
<223> OTHER INFORMATION: PCR reverse primer for LXR-beta ligand binding
      region

<400> SEQUENCE: 10
```

```
ctggatccct cgtggacgtc ccagatct                                          28
```

<210> SEQ ID NO 11
<211> LENGTH: 28
<212> TYPE: DNA
<213> ORGANISM: Artificial Sequence
<220> FEATURE:
<223> OTHER INFORMATION: PCR forward primer for RXR-alpha ligand binding
      region

<400> SEQUENCE: 11

```
ccagatctaa gcgggaagcc gtgcagga                                          28
```

<210> SEQ ID NO 12
<211> LENGTH: 28
<212> TYPE: DNA
<213> ORGANISM: Artificial Sequence
<220> FEATURE:
<223> OTHER INFORMATION: PCR reverse primer for RXR-alpha ligand binding
      region

<400> SEQUENCE: 12

```
ccagatctag tcatttggtg cggcgcct                                          28
```

<210> SEQ ID NO 13
<211> LENGTH: 284
<212> TYPE: PRT
<213> ORGANISM: Artificial Sequence
<220> FEATURE:
<223> OTHER INFORMATION: fusion protein LXR-lapha ligand binding region
      and His-tag

<400> SEQUENCE: 13

Arg Glu Glu Cys Val Leu Ser Glu Glu Gln Ile Arg Leu Lys Lys Leu
1               5                   10                  15

Lys Arg Gln Glu Glu Glu Gln Ala His Ala Thr Ser Leu Pro Pro Arg
            20                  25                  30

Arg Ser Ser Pro Pro Gln Ile Leu Pro Gln Leu Ser Pro Glu Gln Leu
        35                  40                  45

Gly Met Ile Glu Lys Leu Val Ala Ala Gln Gln Gln Cys Asn Arg Arg
    50                  55                  60

Ser Phe Ser Asp Arg Leu Arg Val Thr Pro Trp Pro Met Ala Pro Asp
65                  70                  75                  80

Pro His Ser Arg Glu Ala Arg Gln Gln Arg Phe Ala His Phe Thr Glu
                85                  90                  95

Leu Ala Ile Val Ser Val Gln Glu Ile Val Asp Phe Ala Lys Gln Leu
            100                 105                 110

Pro Gly Phe Leu Gln Leu Ser Arg Glu Asp Gln Ile Ala Leu Leu Lys
        115                 120                 125

Thr Ser Ala Ile Glu Val Met Leu Leu Glu Thr Ser Arg Arg Tyr Asn
    130                 135                 140

Pro Gly Ser Glu Ser Ile Thr Phe Leu Lys Asp Phe Ser Tyr Asn Arg
145                 150                 155                 160

Glu Asp Phe Ala Lys Ala Gly Leu Gln Val Glu Phe Ile Asn Pro Ile
                165                 170                 175

Phe Glu Phe Ser Arg Ala Met Asn Glu Leu Gln Leu Asn Asp Ala Glu
            180                 185                 190

Phe Ala Leu Leu Ile Ala Ile Ser Ile Phe Ser Ala Asp Arg Pro Asn
        195                 200                 205

Val Gln Asp Gln Leu Gln Val Glu Arg Leu Gln His Thr Tyr Val Glu
    210                 215                 220

-continued

```
Ala Leu His Ala Tyr Val Ser Ile His His Pro His Asp Arg Leu Met
225                 230                 235                 240

Phe Pro Arg Met Leu Met Lys Leu Val Ser Leu Arg Thr Leu Ser Ser
                245                 250                 255

Val His Ser Glu Gln Val Phe Ala Leu Arg Leu Gln Asp Lys Lys Leu
            260                 265                 270

Pro Pro Leu Leu Ser Glu Ile Trp Asp Val His Glu
        275                 280

<210> SEQ ID NO 14
<211> LENGTH: 262
<212> TYPE: PRT
<213> ORGANISM: Artificial Sequence
<220> FEATURE:
<223> OTHER INFORMATION: fusion protein RXR-lapha ligand binding region
      and FLAG

<400> SEQUENCE: 14

Lys Arg Glu Ala Val Gln Glu Glu Arg Gln Arg Gly Lys Asp Arg Asn
1               5                   10                  15

Glu Asn Glu Val Glu Ser Thr Ser Ser Ala Asn Glu Asp Met Pro Val
            20                  25                  30

Glu Arg Ile Leu Glu Ala Glu Leu Ala Val Glu Pro Lys Thr Glu Thr
        35                  40                  45

Tyr Val Glu Ala Asn Met Gly Leu Asn Pro Ser Ser Pro Asn Asp Pro
    50                  55                  60

Val Thr Asn Ile Cys Gln Ala Ala Asp Lys Gln Leu Phe Thr Leu Val
65                  70                  75                  80

Glu Trp Ala Lys Arg Ile Pro His Phe Ser Glu Leu Pro Leu Asp Asp
                85                  90                  95

Gln Val Ile Leu Leu Arg Ala Gly Trp Asn Glu Leu Leu Ile Ala Ser
            100                 105                 110

Phe Ser His Arg Ser Ile Ala Val Lys Asp Gly Ile Leu Leu Ala Thr
        115                 120                 125

Gly Leu His Val His Arg Asn Ser Ala His Ser Ala Gly Val Gly Ala
    130                 135                 140

Ile Phe Asp Arg Val Leu Thr Glu Leu Val Ser Lys Met Arg Asp Met
145                 150                 155                 160

Gln Met Asp Lys Thr Glu Leu Gly Cys Leu Arg Ala Ile Val Leu Phe
                165                 170                 175

Asn Pro Asp Ser Lys Gly Leu Ser Asn Pro Ala Glu Val Glu Ala Leu
            180                 185                 190

Arg Glu Lys Val Tyr Ala Ser Leu Glu Ala Tyr Cys Lys His Lys Tyr
        195                 200                 205

Pro Glu Gln Pro Gly Arg Phe Ala Lys Leu Leu Leu Arg Leu Pro Ala
    210                 215                 220

Leu Arg Ser Ile Gly Leu Lys Cys Leu Glu His Leu Phe Phe Phe Lys
225                 230                 235                 240

Leu Ile Gly Asp Thr Pro Ile Asp Thr Phe Leu Met Glu Met Leu Glu
                245                 250                 255

Ala Pro His Gln Met Thr
            260

<210> SEQ ID NO 15
<211> LENGTH: 307
<212> TYPE: PRT
<213> ORGANISM: Artificial Sequence
```

<220> FEATURE:
<223> OTHER INFORMATION: fusion protein LXR-beta ligand binding region and His-tag

<400> SEQUENCE: 15

```
Arg Glu Gln Cys Val Leu Ser Glu Gln Ile Arg Lys Lys Ile
1               5                   10                  15

Arg Lys Gln Gln Gln Glu Ser Gln Ser Gln Ser Pro Val
            20                  25                  30

Gly Pro Gln Gly Ser Ser Ser Ala Ser Gly Pro Gly Ala Ser Pro
        35                  40                  45

Gly Gly Ser Glu Ala Gly Ser Gly Ser Gly Glu Gly Val
50                  55                  60

Gln Leu Thr Ala Ala Gln Glu Leu Met Ile Gln Gln Leu Val Ala Ala
65                  70                  75                  80

Gln Leu Gln Cys Asn Lys Arg Ser Phe Ser Asp Gln Pro Lys Val Thr
                85                  90                  95

Pro Trp Pro Leu Gly Ala Asp Pro Gln Ser Arg Asp Ala Arg Gln Gln
                100                 105                 110

Arg Phe Ala His Phe Thr Glu Leu Ala Ile Ile Ser Val Gln Glu Ile
                115                 120                 125

Val Asp Phe Ala Lys Gln Val Pro Gly Phe Leu Gln Leu Gly Arg Glu
130                 135                 140

Asp Gln Ile Ala Leu Leu Lys Ala Ser Thr Ile Glu Ile Met Leu Leu
145                 150                 155                 160

Glu Thr Ala Arg Arg Tyr Asn His Glu Thr Glu Cys Ile Thr Phe Leu
                165                 170                 175

Lys Asp Phe Thr Tyr Ser Lys Asp Asp Phe His Arg Ala Gly Leu Gln
                180                 185                 190

Val Glu Phe Ile Asn Pro Ile Phe Glu Phe Ser Arg Ala Met Arg Arg
                195                 200                 205

Leu Gly Leu Asp Asp Ala Glu Tyr Ala Leu Leu Ile Ala Ile Asn Ile
                210                 215                 220

Phe Ser Ala Asp Arg Pro Asn Val Gln Glu Pro Gly Arg Val Glu Ala
225                 230                 235                 240

Leu Gln Gln Pro Tyr Val Glu Ala Leu Leu Ser Tyr Thr Arg Ile Lys
                245                 250                 255

Arg Pro Gln Asp Gln Leu Arg Phe Pro Arg Met Leu Met Lys Leu Val
                260                 265                 270

Ser Leu Arg Thr Leu Ser Ser Val His Ser Glu Gln Val Phe Ala Leu
                275                 280                 285

Arg Leu Gln Asp Lys Lys Leu Pro Pro Leu Leu Ser Glu Ile Trp Asp
290                 295                 300

Val His Glu
305
```

<210> SEQ ID NO 16
<211> LENGTH: 25
<212> TYPE: PRT
<213> ORGANISM: Homo sapiens

<400> SEQUENCE: 16

```
Asp Gly Thr Pro Pro Gln Glu Ala Glu Pro Ser Leu Leu Lys
1               5                   10                  15

Lys Leu Leu Leu Ala Pro Ala Asn Thr
            20                  25
```

```
<210> SEQ ID NO 17
<211> LENGTH: 25
<212> TYPE: PRT
<213> ORGANISM: Homo sapiens

<400> SEQUENCE: 17

His Gly Thr Ser Leu Lys Glu Lys His Lys Ile Leu His Arg Leu Leu
1               5                   10                  15

Gln Asp Ser Ser Ser Pro Val Asp Leu
            20                  25

<210> SEQ ID NO 18
<211> LENGTH: 30
<212> TYPE: PRT
<213> ORGANISM: Homo sapiens

<400> SEQUENCE: 18

Asn Lys Asp Val Thr Leu Thr Ser Pro Leu Leu Val Asn Leu Leu Gln
1               5                   10                  15

Ser Asp Ile Ser Ala Gly His Phe Gly Val Asn Asn Lys Gln
            20                  25                  30

<210> SEQ ID NO 19
<211> LENGTH: 30
<212> TYPE: PRT
<213> ORGANISM: Homo sapiens

<400> SEQUENCE: 19

Ser Pro Ala Met Arg Glu Ala Pro Thr Ser Leu Ser Gln Leu Leu Asp
1               5                   10                  15

Asn Ser Gly Ala Pro Asn Val Thr Ile Lys Pro Pro Gly Leu
            20                  25                  30

<210> SEQ ID NO 20
<211> LENGTH: 25
<212> TYPE: PRT
<213> ORGANISM: Homo sapiens

<400> SEQUENCE: 20

Cys Pro Ser Ser His Ser Ser Leu Thr Glu Arg His Lys Ile Leu His
1               5                   10                  15

Arg Leu Leu Gln Glu Gly Ser Pro Ser
            20                  25

<210> SEQ ID NO 21
<211> LENGTH: 20
<212> TYPE: PRT
<213> ORGANISM: Homo sapiens

<400> SEQUENCE: 21

Lys Glu Ser Lys Asp His Gln Leu Leu Arg Tyr Leu Leu Asp Lys Asp
1               5                   10                  15

Glu Lys Asp Leu
            20

<210> SEQ ID NO 22
<211> LENGTH: 24
<212> TYPE: PRT
<213> ORGANISM: Homo sapiens

<400> SEQUENCE: 22

Gln Lys Pro Thr Ser Gly Pro Gln Thr Pro Gln Ala Gln Gln Lys Ser
1               5                   10                  15
```

```
Leu Leu Gln Gln Leu Leu Thr Glu
            20

<210> SEQ ID NO 23
<211> LENGTH: 25
<212> TYPE: PRT
<213> ORGANISM: Homo sapiens

<400> SEQUENCE: 23

Cys Cys Phe Cys Gly Glu Asp His Pro Arg Gln Gly Ser Ile Leu Tyr
1               5                   10                  15

Ser Leu Leu Thr Ser Ser Lys Gln Thr
            20                  25

<210> SEQ ID NO 24
<211> LENGTH: 25
<212> TYPE: PRT
<213> ORGANISM: Homo sapiens

<400> SEQUENCE: 24

Lys Asn Pro Thr Ser Cys Ser Arg Arg Phe Tyr Gln Leu Thr Lys Leu
1               5                   10                  15

Leu Asp Ser Val Gln Pro Ile Ala Arg
            20                  25

<210> SEQ ID NO 25
<211> LENGTH: 25
<212> TYPE: PRT
<213> ORGANISM: Homo sapiens

<400> SEQUENCE: 25

Lys Gln Glu Pro Val Ser Pro Lys Lys Lys Glu Asn Ala Leu Leu Arg
1               5                   10                  15

Tyr Leu Leu Asp Lys Asp Asp Thr Lys
            20                  25

<210> SEQ ID NO 26
<211> LENGTH: 25
<212> TYPE: PRT
<213> ORGANISM: Homo sapiens

<400> SEQUENCE: 26

Gly His Gly Glu Asp Phe Ser Lys Val Ser Gln Asn Pro Ile Leu Thr
1               5                   10                  15

Ser Leu Leu Gln Ile Thr Gly Asn Gly
            20                  25

<210> SEQ ID NO 27
<211> LENGTH: 23
<212> TYPE: PRT
<213> ORGANISM: Homo sapiens

<400> SEQUENCE: 27

His Ser Lys Ala Ser Trp Ala Glu Phe Ser Ile Leu Arg Glu Leu Leu
1               5                   10                  15

Ala Gln Asp Val Leu Cys Asp
            20

<210> SEQ ID NO 28
<211> LENGTH: 26
<212> TYPE: PRT
<213> ORGANISM: Homo sapiens
```

-continued

```
<400> SEQUENCE: 28

Ser Pro Lys Lys Lys Glu Asn Asn Ala Leu Leu Arg Tyr Leu Leu Asp
1               5                   10                  15

Arg Asp Asp Pro Ser Asp Ala Leu Ser Lys
            20                  25
```